(12) United States Patent
Chu et al.

(10) Patent No.: US 11,890,210 B2
(45) Date of Patent: Feb. 6, 2024

(54) DEVICES, SYSTEMS, AND METHODS FOR DELIVERING A STENT

(71) Applicant: Boston Scientific Scimed, Inc., Maple Grove, MN (US)

(72) Inventors: Michael S H Chu, Brookline, MA (US); Mayur K. Patel, Framingham, MA (US); Sacha Tang, Lowell, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 492 days.

(21) Appl. No.: 16/999,882

(22) Filed: Aug. 21, 2020

(65) Prior Publication Data
US 2021/0052403 A1 Feb. 25, 2021

Related U.S. Application Data

(60) Provisional application No. 62/890,832, filed on Aug. 23, 2019.

(51) Int. Cl.
*A61F 2/88* (2006.01)
*A61F 2/95* (2013.01)
(Continued)

(52) U.S. Cl.
CPC .................. *A61F 2/88* (2013.01); *A61F 2/04* (2013.01); *A61F 2/9517* (2020.05); *A61F 2/966* (2013.01);
(Continued)

(58) Field of Classification Search
CPC ........ A61F 2/88; A61F 2/04; A61F 2002/048; A61F 2250/0007; A61F 2/07; A61F 2/885; A61M 27/008
See application file for complete search history.

(56) References Cited

U.S. PATENT DOCUMENTS 5,647,843 A 7/1997 Mesrobian et al.
2002/0062148 A1 5/2002 Hart
(Continued)

FOREIGN PATENT DOCUMENTS

DE 4134030 A1 4/1993
EP 2977075 B1 * 6/2019 ............... A61F 2/94

OTHER PUBLICATIONS

International Search Reportand Written Opinion for the International Patent Application No. PCT/US2020/047456, dated Jan. 15, 2021, 22 pages.
(Continued)

*Primary Examiner* — Keri J Nelson
*Assistant Examiner* — Rebecca Lynee Zimmerman
(74) *Attorney, Agent, or Firm* — Seager, Tufte & Wickhem, LLP

(57) ABSTRACT

The present disclosure relates generally to the field of medical devices. In particular, the present disclosure relates to delivering a variable length stent within a patient. In one example, a stent may include a body comprising coils about a longitudinal axis of the stent and along the length of the stent between a proximal end and a distal end in a substantially helical pattern. The coils may define a lumen along the longitudinal axis through the center of the body. A distal tube may have a wall extending from the distal end of the body. A first aperture may extend through the wall of the distal tube into the lumen. A distal retention member may extend from the distal tube. A distal suture may have a mid-portion. The mid-portion may extend through the first aperture.

13 Claims, 12 Drawing Sheets

(51) Int. Cl.
*A61F 2/04* (2013.01)
*A61F 2/966* (2013.01)

(52) U.S. Cl.
CPC . *A61F 2002/048* (2013.01); *A61F 2210/0014* (2013.01); *A61F 2220/0008* (2013.01); *A61F 2250/0007* (2013.01); *A61F 2250/0098* (2013.01)

(56) References Cited

U.S. PATENT DOCUMENTS

| | | | |
|---|---|---|---|
| 2004/0087886 A1* | 5/2004 | Gellman | A61M 27/008 604/8 |
| 2007/0270937 A1 | 11/2007 | Leanna | |
| 2014/0236280 A1 | 8/2014 | Havel | |
| 2016/0113787 A1 | 4/2016 | Biltz et al. | |
| 2017/0056154 A1 | 3/2017 | Greenberg et al. | |
| 2017/0165067 A1 | 6/2017 | Barajas-Torres et al. | |
| 2020/0121442 A1* | 4/2020 | Askeland | A61M 27/008 |

OTHER PUBLICATIONS

Brotherhood, Hilary, Dirk Lange, & Ben H. Chew. "Advances in ureteral stents." Translational Andrology and Urology [Online], 3.3 (2014): 314-319. Web. Apr. 14, 2021.
Percuflex™ Ureteral Stent—Boston Scientific—URO-168423-AC Jan. 2018—URL: https://www.bostonscientific.com/content/gwc/en-US/products/stents-ureteral/percuflex.html.
SureDrive™ Steerable Ureteral Stent—Boston Scientific—URO-381301-AA Mar. 2016—URL: https://www.bostonscientific.com/en-EU/products/stents-ureteral/SureDrive-steerable-ureteral-stent.html#latexInformation.

* cited by examiner

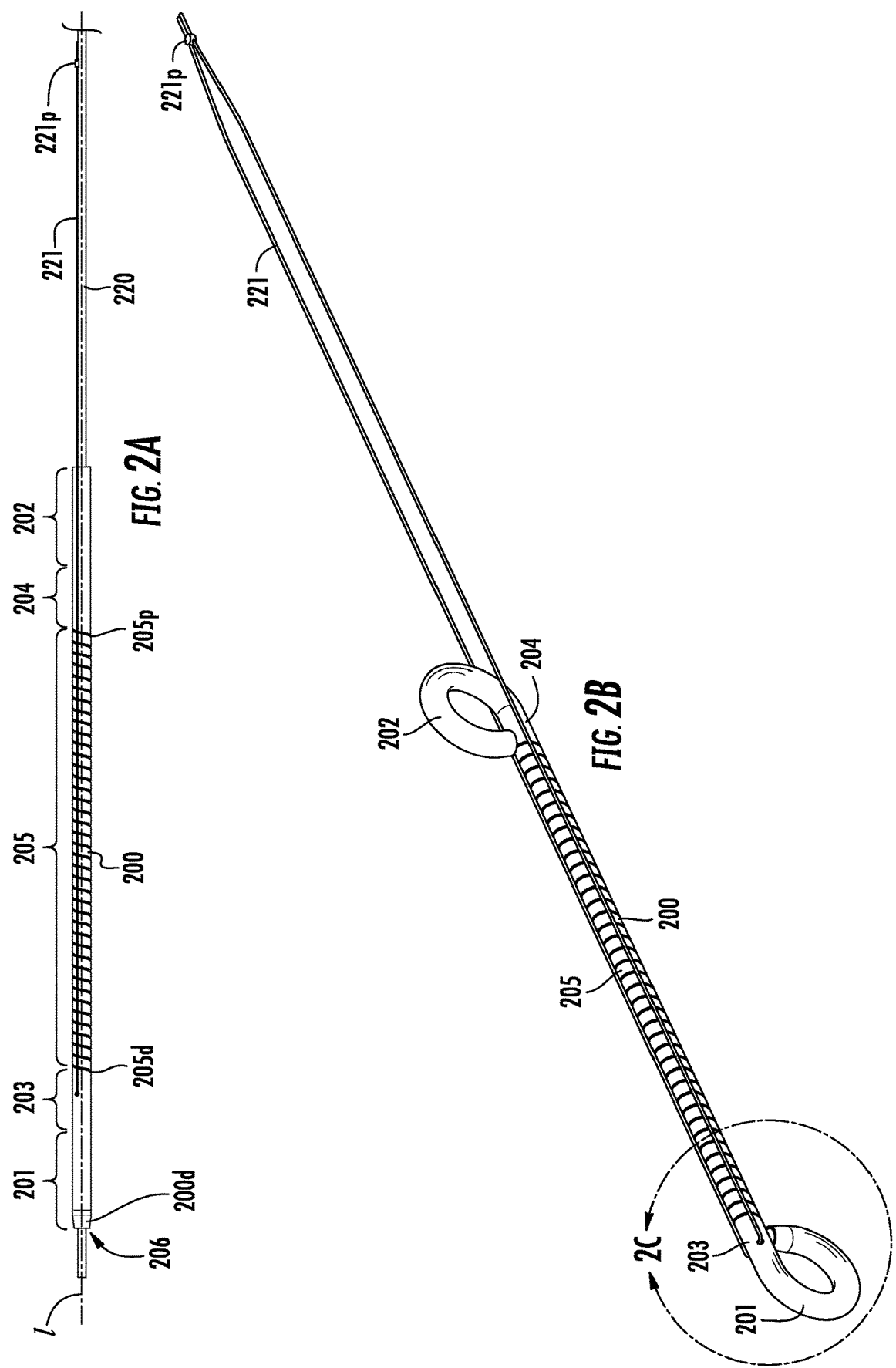

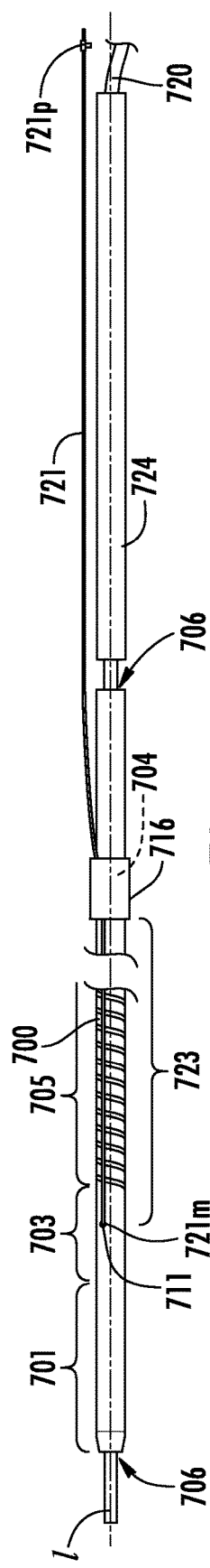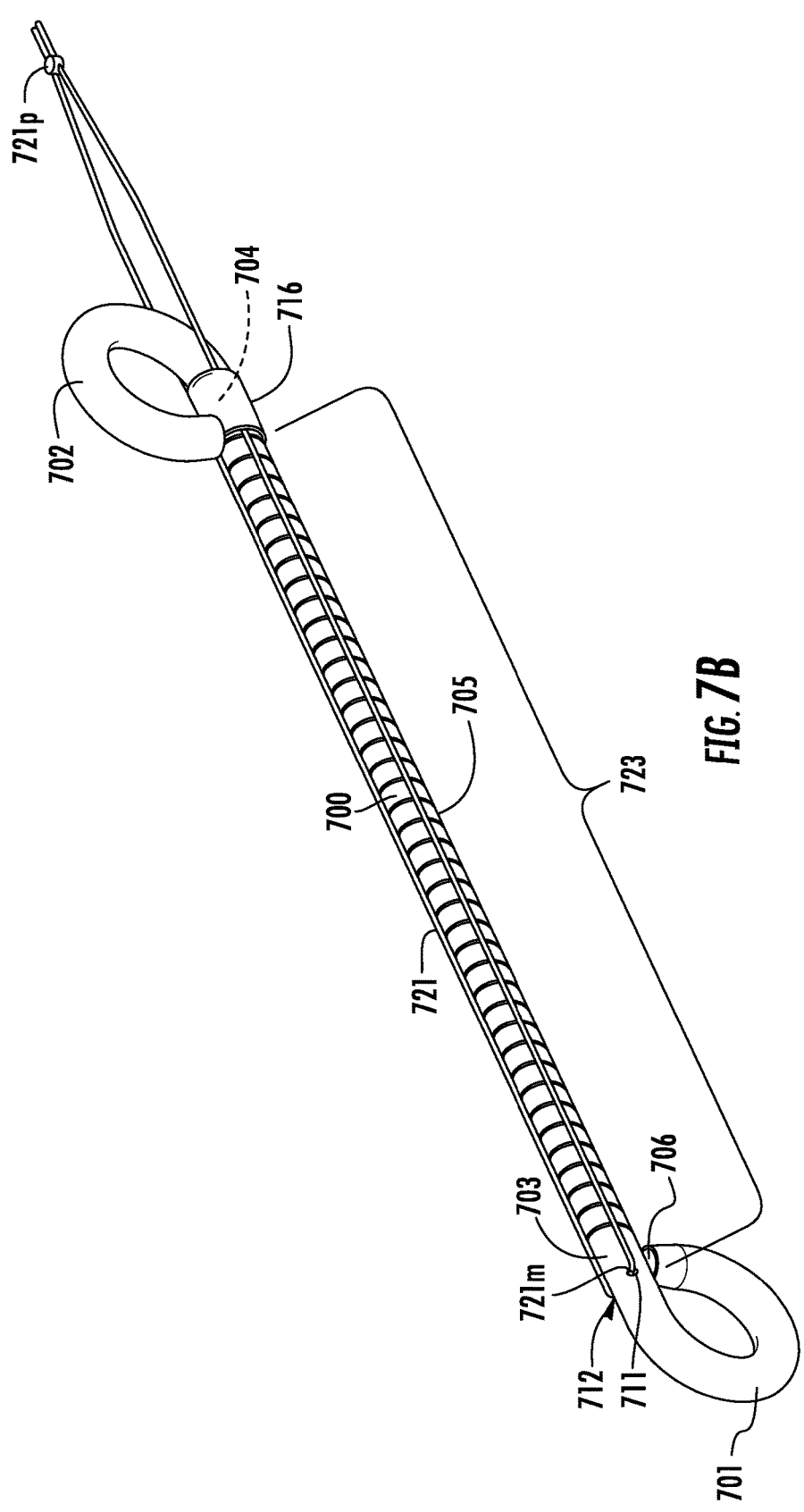
FIG. 7A
FIG. 7B

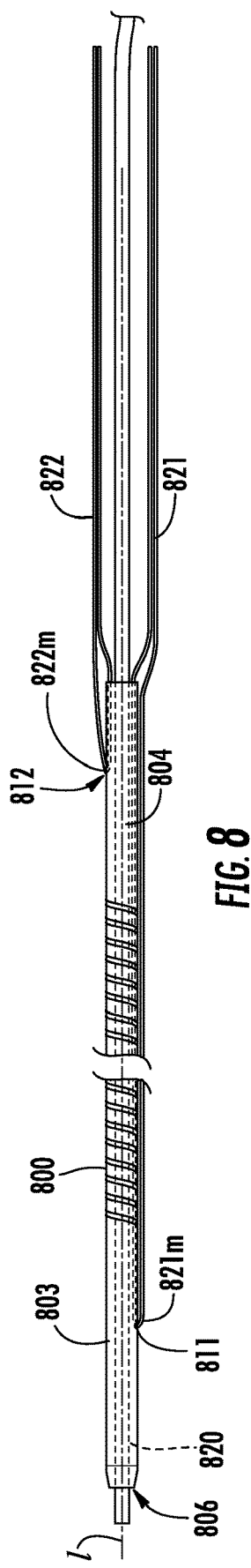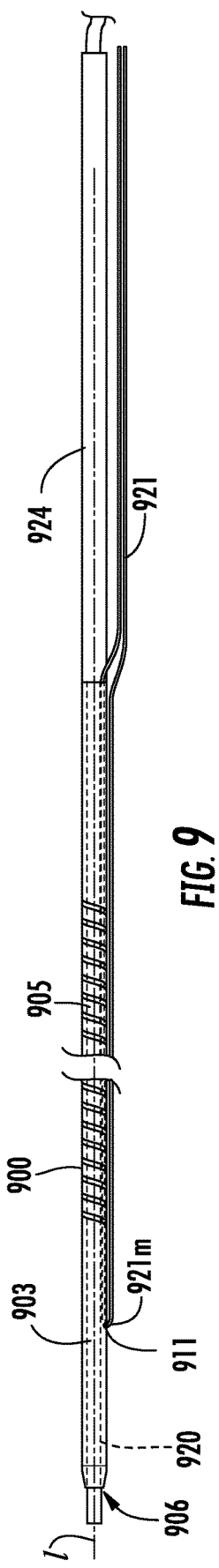

DEVICES, SYSTEMS, AND METHODS FOR DELIVERING A STENT

PRIORITY

This application claims the benefit of priority under 35 USC § 119 to U.S. Provisional Patent Application Ser. No. 62/890,832, filed Aug. 23, 2019 and titled "Devices, Systems, and Methods for Delivering a Stent," the disclosures of which are incorporated by reference herein in their entirety and for all purposes.

FIELD

The present disclosure relates generally to the field of medical devices. In particular, the present disclosure relates to devices, systems and methods for delivering a variable length stent within a patient.

BACKGROUND

Delivered stents having a fixed length that may be too short for a patient's anatomy and may need to be withdrawn and replaced with a new stent, potentially prolonging a procedure and increasing the chance of complications. Delivered stents having a fixed length that is too long for a patient's anatomy may cause irritation due to the excess length having to be accommodated in the body, e.g., within the bladder in the case of a ureteral stent. Variable length stents may present delivery, positioning, repositioning, length adjustment, disengagement challenges associated with the length of body of the stent being adjustable. For example, even if the desired length is correct at the time of positioning the stent, a variable length stent may undesirably, prematurely or improperly extend or compress in length during placement, repositioning and/or removal.

It is with these considerations in mind that the improvements of the present disclosure may be useful.

SUMMARY

The present disclosure, in its various aspects, is directed generally to medical devices, and particularly variable length stents and devices, systems and method for delivering such stents, e.g., ureteral stents. In an aspect, a stent may include a body comprising coils about a longitudinal axis of the stent and along the length of the stent between a proximal end and a distal end in a substantially helical pattern. The coils may define a lumen along the longitudinal axis through the center of the body. A distal tube having a wall may extend distally from the distal end of the body. The lumen may extend through the distal tube. A first aperture may extend through the wall of the distal tube into the lumen. A proximal tube having a wall may extend proximally from the proximal end of the body. The lumen may extend through the proximal tube. A distal retention member may extend distally from the distal tube. The lumen may extend through the distal retention member. A proximal retention member having a wall may extend proximally from the proximal tube to a proximal end of the proximal retention member. The lumen may extend through the proximal retention member to the proximal end of the proximal retention member. A distal suture may have a first end, a second end, and a mid-portion. The mid-portion may extend through the first aperture.

In various embodiments described here or otherwise, a second aperture may extend through the wall of the distal tube into the lumen such that the first aperture and the second aperture are aligned forming a suture axis that is offset from the longitudinal axis. The mid-portion of the distal suture may extend through the second aperture. A third aperture may extend through the wall of the proximal retention member into the lumen. A proximal suture may have a first end, a second end, and a mid-portion. The mid-portion may extend through the third aperture and the proximal end of the proximal retention member. A portion of the distal suture may be adhered to the proximal tube. A fourth aperture may extend through the wall of the distal tube into the lumen such that the first aperture and the fourth aperture may be aligned parallel to the longitudinal axis. The mid-portion of the distal suture may extend through the fourth aperture. A fifth aperture may extend through the wall of the distal tube into the lumen such that the first aperture and the fifth aperture are aligned forming a suture axis that intersects the longitudinal axis. The mid-portion of the distal suture may extend through the fifth aperture. The distal suture from the first end may extend distally within the lumen along the wall of the distal tube, through the first aperture, along an outside surface of the wall of the distal tube, through the fifth aperture into the lumen, and proximally along the wall of the distal tube within the lumen to the second end. A pre-set gap may be between select adjacent coils of the body. The gap may be configured such that a diameter of the lumen increases as the select adjacent coils are compressed together along the longitudinal axis. Axial compression of the body may be controllable by applying proximal tension to the distal suture. The proximal and distal retention members may be in the shape of a pigtail, a J-shaped curve, a cope loop, a spiral shape, a helical shape, or a cork screw, or a combination thereof. The distal retention member may have a tapered distal tip, tapering distally.

In an aspect, a stent delivery system may include a stent delivery device. The stent delivery device may include a cannula having a proximal end, a distal end, and a cannula lumen therethrough. A handle may be at the proximal end of the cannula. A pusher may be disposed over the cannula. The pusher may have a proximal end, a distal end, and a pusher lumen therethrough. A locking knob may be at the proximal end of the pusher and reversibly coupled to the handle. A stent may include a body comprising coils and disposed over the cannula, the stent having a stent lumen through a length of the stent. The distal end of the cannula may be reversibly engageable with a portion of the length of the stent.

In various embodiments described here or otherwise, the portion of the stent may be proximal to a ring portion of the stent disposed within the stent lumen on a wall of the stent. The portion of the stent may be distal to a distally tapering portion within the stent lumen on the wall of the stent. The cannula may have an outer diameter larger than a diameter of the stent lumen. The portion of the length of the stent may be along a proximal end of the stent. The cannula may have an outer diameter larger than a diameter of the stent lumen and the portion of the length of the stent may be along a distal end of the stent. A guidewire may be disposed through the cannula lumen.

In an aspect, a method for positioning a stent may include inserting a guidewire to a target position within a patient. A stent may be inserted including a body comprising coils over the guidewire. The stent may be distally translated within the patient over the guidewire via a pusher. The stent may be proximally translated within the patient over the guidewire via a first suture associated with a distal portion of the stent. Distally translating the stent may include pushing the stent with the pusher. The stent may be proximally translated by applying tension to the first suture.

In various embodiments described here or otherwise, a length of the stent may be adjusted within the patient by adjusting a gap between select body wound coils of the stent. The stent may be removed from the patient by translating a second suture disposed through a proximal portion of the stent.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures:

FIG. 2A illustrates a stent in a delivery configuration, in accordance with an embodiment of the present disclosure.

FIG. 2B illustrates the stent of FIG. 2A in a deployed configuration.

FIG. 7A illustrates a stent system with a stent in a delivery configuration, in accordance with an embodiment of the present disclosure.

FIG. 7B illustrates the stent of FIG. 7A in a deployed configuration.

FIG. 8 illustrates a stent system with a stent in a delivery configuration, in accordance with an embodiment of the present disclosure.

FIG. 9 illustrates a stent system with a stent in a delivery configuration, in accordance with an embodiment of the present disclosure.

Figure 1:
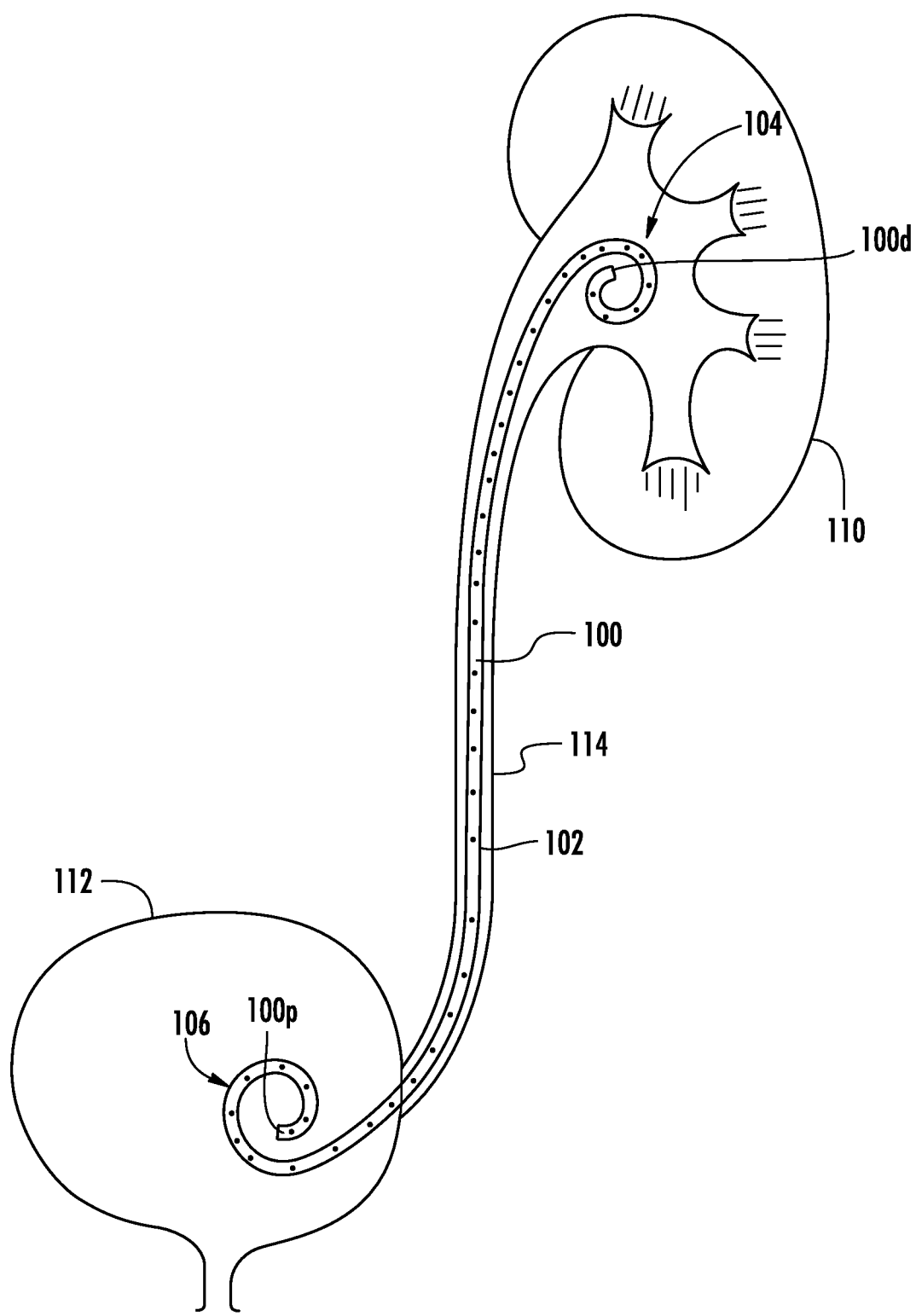
FIG. 1 is an illustration of a prior art ureteral stent, positioned in a ureter between the kidney and the bladder.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

The present disclosure is not limited to the embodiments described. The terminology used herein is only for the purpose of describing particular embodiments and is not intended to be limiting. Unless otherwise defined, all technical terms used herein have the same meaning as commonly understood by one of ordinary skill in the art to which the disclosure belongs.

Although embodiments of the present disclosure may be described with specific reference to ureteral stents, it should be appreciated that such devices, systems, and methods may be used with a variety of instruments and for a variety of other tissues, body passageways, organs and/or cavities, such as the vascular system, urogenital system, upper gastrointestinal system, lower gastrointestinal system, and the like.

As used herein, a "proximal" end refers to the end of a device that lies closest to the medical professional along the device when introducing the device into a patient, and a "distal" end refers to the end of a device or object that lies furthest from the medical professional along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g., 1 to 5 includes 1, 1.5, 2, 2.75, 3, 3.80, 4, and 5).

As used herein, the conjunction "and" includes each of the structures, components, portions, or the like, which are so conjoined, unless the context clearly indicates otherwise, and the conjunction "or" includes one or the others of the structures, components, portions, or the like, which are so conjoined, singly and in any combination and number, unless the context clearly indicates otherwise.

The detailed description should be read with reference to the drawings, which are not necessarily to scale, depict illustrative embodiments, and are not intended to limit the scope of the invention.

Stents may be delivered into patients for various purposes including stenting, drainage, etc., of lumens, tracts, vessels, and cavities within the body. As an example, ureteral stents may be used to facilitate drainage in the upper urinary tract (e.g., drainage from the kidney to the bladder), possibly following ureteroscopy, endouretotomies, and endopyelotomy, as well as in other instances where ureteral obstruction may occur or access to the kidney and/or ureter is otherwise warranted.

An exemplary stent 100 of this type is illustrated in FIG. 1. The stent 100 has a proximal end 100p and a distal end 100d. It is a tubular polymer extrusion having a shaft 102, a distal renal retention member (e.g., renal "pigtail" 104), and a proximal retention member (e.g., bladder "pigtail" 106). These retention members 104, 106 prevent upward migration of the stent 100 toward the kidney 110 or downward migration of the stent 100 toward the bladder 112. Once properly deployed in the ureter 114, the stent 100 supports the ureter 114 and allows the passage of urine through the stent 100 and, because the ureter 114 naturally dilates around foreign bodies, allows urine to flow around the stent 100 as well.

In various embodiments of a stent described herein and otherwise within the scope of the present disclosure, a stent may be placed over a guidewire, through a cystoscope, a flexible ureteroscope, or the like, and advanced into a position with a delivery device that may engage and may release the stent. Once the distal end of the stent is advanced into the kidney/renal calyx, the guidewire and/or delivery device are removed, allowing retention members, such as pigtails to form in the kidney and bladder. The distal retention member of a stent may be closed or tapered on the end, which may depend on the method of insertion (e.g., the use of a guidewire or otherwise).

A delivered stent may cause patient discomfort or pain, for example, regarding ureteral stents, pain and/or discomfort in the bladder and flank area after insertion, particularly if the delivered length of the stent is not well-suited to the anatomy of the patient. Various applications and anatomies therefore may benefit from stents of different diameters and lengths, e.g., differences in individual ureteral anatomies require different diameters and lengths between the end retention members of ureteral stents. Stents that are variable in length address various of these concerns, but also present challenges of their own, e.g., efficiently and accurately controlling the delivery, positioning and removal of stents that can be extended and contracted in length, such as stents having a body comprising coils.

Figure 2C:
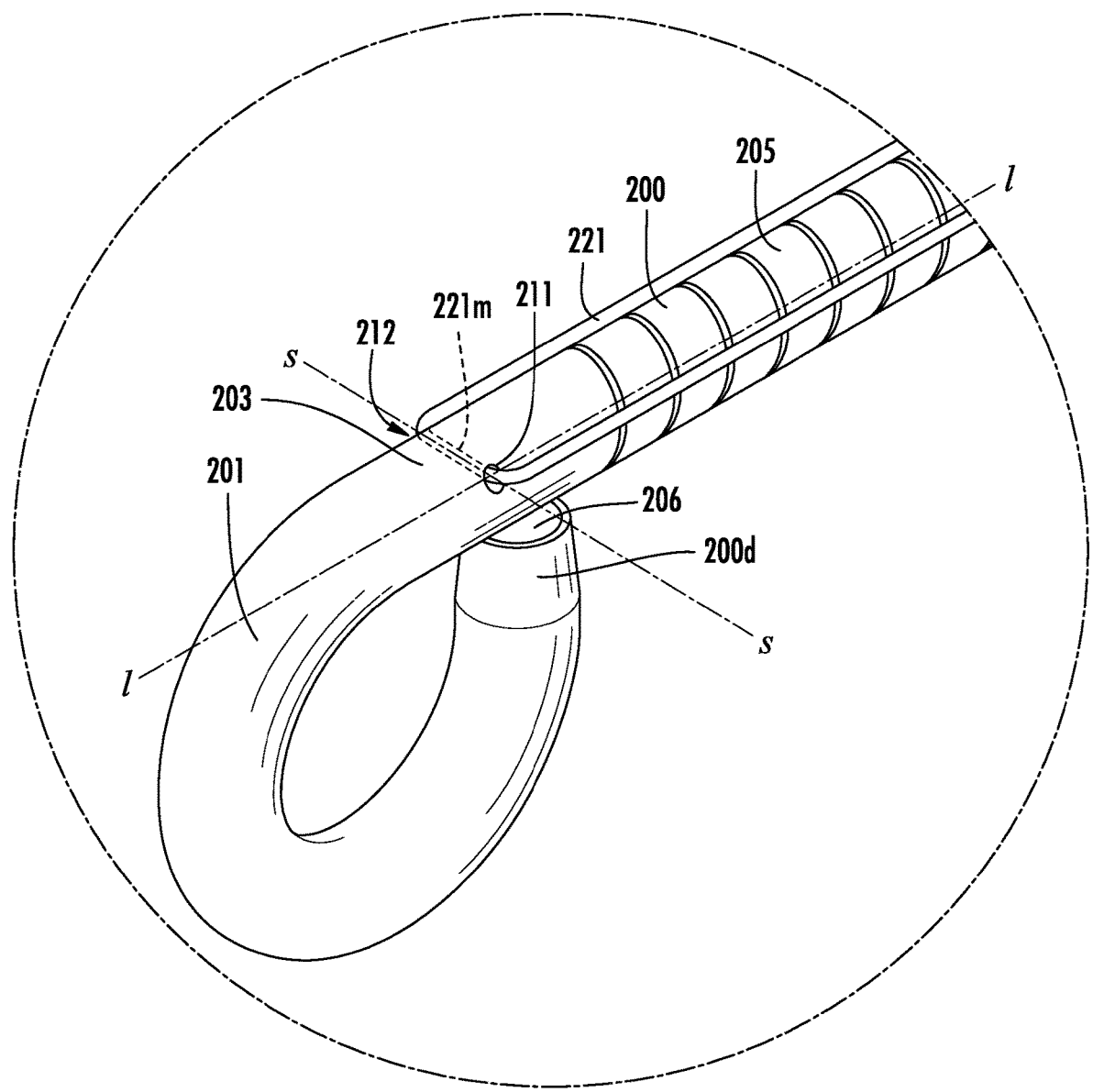
FIG. 2C illustrates a distal portion of the stent of FIG. 2B.

Referring to FIGS. 2A-2C, a stent 200 according to an embodiment of the present disclosure is illustrated. In FIG. 2A, the stent 200 is in a delivery configuration arranged over a guidewire 220 extending through a lumen 206 of the stent 200, thereby substantially extending (i.e., straightening) a distal retention member 201 and a proximal retention member 202. The guidewire 220 is sufficiently stiff to hold the retention members 201, 202 substantially straight along a longitudinal axis $\ell$ during delivery through a body lumen of a patient, e.g., a ureteral stent delivered within a ureter between a kidney and the bladder of the patient. The stent 200 includes a body 205 wound in coils about the longitudinal axis $\ell$ of the stent 200. The body 205 extends along a length of the stent 200 between a distal end 205d and a proximal end 205p in a substantially helical pattern. Various other patterns, shapes, widths, pitches, etc., for coils may be utilized, as desired, for a particular application. The body 205 defines the lumen 206 along the longitudinal axis $\ell$ through the center of the helical pattern. A distal tube 203 extends from the distal end 205d of the body 205, and a proximal tube 204 extends from the proximal end 205p of the body 205. Each of the distal tube 203 and proximal tube 204 further extend the lumen 206 through the tubes 203, 204. The distal retention member 201 extends from the distal tube 203 and the proximal retention member 202 extends from the proximal tube 204. Each of the retention members 201, 202 further extend the lumen 206 through the retention members 201, 202. The distal end 200d of the stent 200 has a distally tapering wall that decreases in diameter such that the distal end 200d may be easier to distally navigate the anatomy of a patient while the stent 200 is in the delivery configuration on the guidewire 220 or other delivery device. Other configurations of tips for the distal and/or proximal retention member 202 may be contemplated. The stent 200 is illustrated in a deployed configuration in FIGS. 2B and 2C with the guidewire 220 removed from the lumen 206, allowing the retention members 201, 202 to form. A first aperture 211 and a second aperture 212 each extend through a wall of the distal tube 203 into the lumen 206. A suture 221 extends along the stent 200 and is configured for a medical professional to deliver, position, reposition, remove, compress, or extend the stent 200. A mid-portion 221m of the suture 221 extends through the first aperture 211 and the second aperture 212. The first aperture 211 and the second aperture 212 are aligned forming a suture axis $\mathcal{S}$ that is offset from (i.e., does not intersect with) the longitudinal axis $\ell$, such that there is little to no contact between the suture 221 and the guidewire 220 than if the two axes intersected. In various embodiments, one or more sutures may extend within a channel extending along a wall of a stent and/or one or more sutures may extend along a separate tubular channel independent of a stent lumen. Ends 221p of the suture 221 are coupled to each other such that a medical professional may more easily manipulate the ends 221p of the suture 221 (e.g., with the medical professional's hand, a handle of a device, or the like) by exerting tension or releasing tension on the suture 221. Ends of the suture in other embodiments may be uncoupled.

The stent 200 and a delivery device, e.g., a pusher (not illustrated), may be loaded onto the guidewire 220 external to the body. The distal retention member 201 may be substantially straightened and back-loaded onto the proximal end of the guidewire 220. The stent 200 may be pushed distally (i.e., rather than pulled) onto the guidewire 220 to minimize the stent 200 extending and/or binding to the guidewire 220. For example, one hand of the medical professional may grip a distal portion of the unloaded stent 200 with the thumb and forefinger and then push the stent 200 with a controlled amount of force to maintain the formation of the stent 200 onto the proximal end of the guidewire 220 or until the guidewire 220 is felt in the lumen 206 by the hand. The thumb and forefinger may be repositioned, e.g., "inched," proximally on another unloaded portion of the stent 200 to further push the stent 200 onto the guidewire 220. Once the stent 200 is sufficiently loaded onto the guidewire 220, the stent 200 may be gripped at the proximal end to advance it further along the guide wire 220. One hand of the medical professional may be used to push the stent 200 while a second hand may be used to steady the guidewire 220. The distal end of the pusher may be loaded onto the proximal end of the guidewire 220 by pushing or pulling the pusher distally until the distal end of the pusher abuts to the proximal end of the stent 200. To advance the stent 200, one hand may grip the proximal end of the guidewire 220 and the second hand may advance the pusher to advance the stent 200 distally into the body and, e.g., into the kidney. The pusher compresses the body 205 while distally translating the stent 200 along the guidewire 220 to maintain or increase the stent lumen 206 inner diameter at the body 205 to reduce binding of the stent 200 to the guidewire 220. The distal retention member 201 resists this distal translation of the stent 200 because the distal retention member 201 tends to partially form into its deployed configuration out of alignment with the longitudinal axis $\ell$ such that it engages the guidewire 220. To reposition the stent 200, e.g., to position the distal retention member 201 in the kidney, the stent 200 may need to be translated proximally by one hand gripping the proximal end of the guidewire 220 while the second hand proximally pulls on the suture 221. When proximally pulled, the suture 221 compresses the body 205 to maintain or increase the stent lumen 206 inner diameter with the proximal retention member 202 resisting proximal translation of the stent 200 because the proximal retention member 202 tends to partially form into its deployed configuration out of alignment with the longitudinal axis $\ell$ such that it engages the guidewire 220. To form the distal retention member 201, the stent 200 may first be translated distally and proximally over the guidewire 220 as desired to position the distal retention member 201. Once satisfied with an initial placement, the pusher may be held stationary with one hand, abutting the proximal end of the stent 200 as the second hand moves guidewire 220 proximally out of the distal retention member 201 to allow the distal retention member 201 to form. A formed distal retention member 201 may be positioned in the kidney by using the first hand to proximally pull the suture 221 and/or by pushing the stent 200 with the pusher in the distal direction over the guidewire 220 while holding the guidewire 220 with the second hand. To inspect the deployed length of the stent 200 (e.g., in comparison with a length of the ureter) one or more radiopaque markers may be viewed under fluoroscopy and their locations may be compared to other markers or anatomies, as discussed below. With the distal retention member 201 formed, the guidewire 220 may still straighten the proximal retention member 202 in the delivery configuration. The pusher may be held abutting the proximal end of the stent 200 and the distal suture 221 can be released from the stent 200. The proximal retention member 202 may be formed by withdrawing the guidewire 220 from the lumen 206, possibly with the pusher held abutting the proximal end of the stent 200.

Figure 3A:
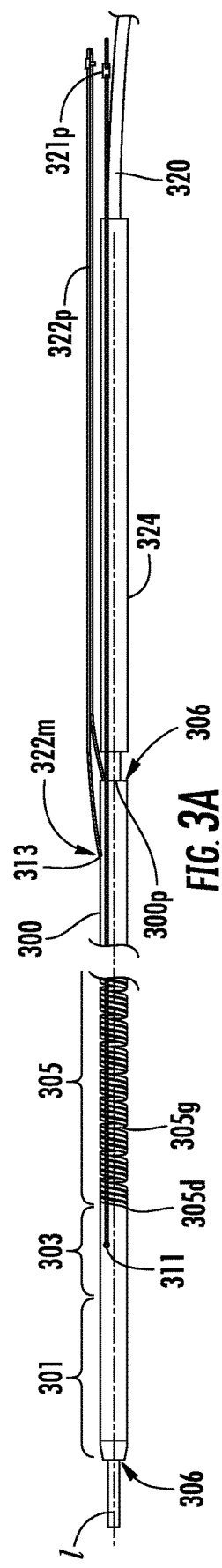
FIG. 3A illustrates a stent in a delivery configuration having groups of adjacent wound coils separated by gaps, in accordance with an embodiment of the present disclosure.
Figure 3B:
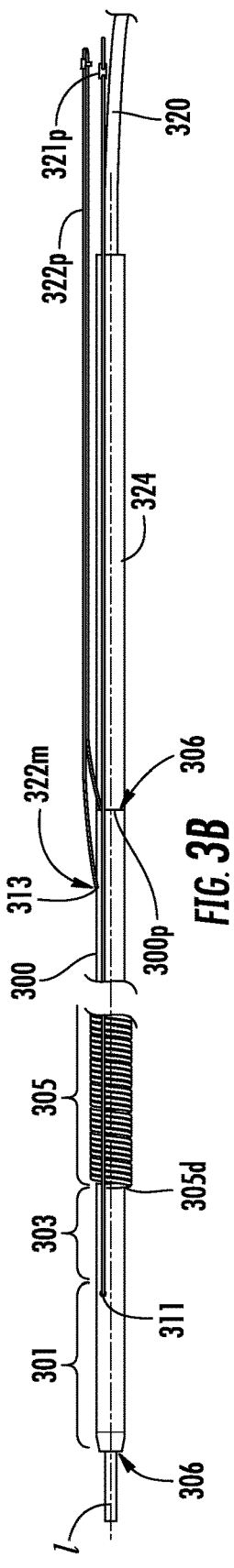
FIG. 3B illustrates the stent of FIG. 3A in a compressed delivery configuration.
Figure 3C:
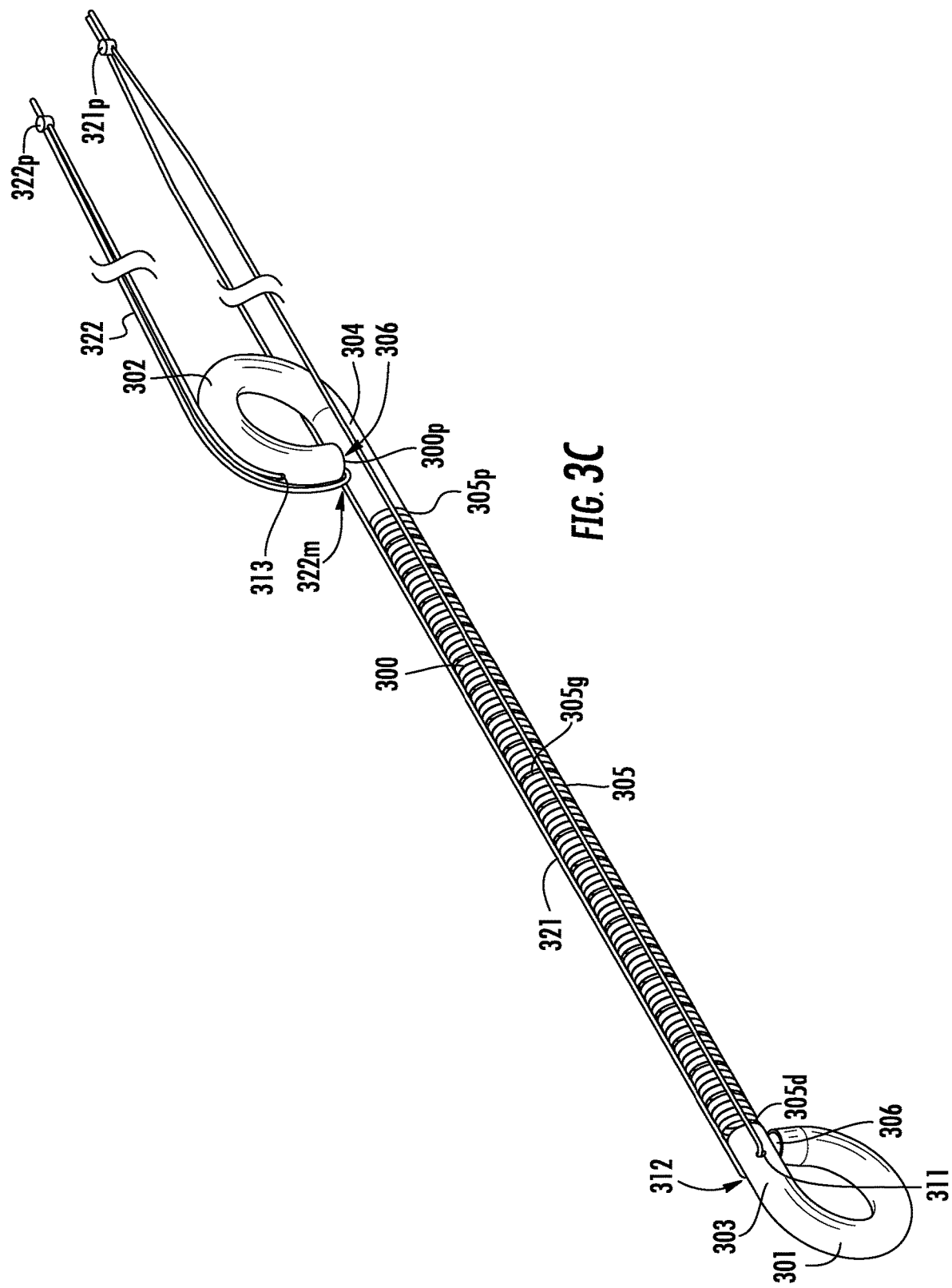
FIG. 3C illustrates the stent of FIGS. 3A and 3B in a deployed configuration.

Referring to FIGS. 3A-3C, a stent 300 according to an embodiment of the present disclosure is illustrated. In FIG. 3A, the stent 300 is in a delivery configuration arranged over a guidewire 320 extending through a lumen 306 of the stent 300, thereby substantially straightening a distal retention member 301 and a proximal retention member 302, each extending from a distal tube 303 and a proximal tube 304, respectfully. The stent 300 includes a body 305 wound in coils about a longitudinal axis $\ell$ of the stent 300. The body 305 extends along a length of the stent 300 between a distal end 305*d* and a proximal end 305*p* in a substantially helical pattern. The body 305 defines a lumen 306 along the longitudinal axis $\ell$ through the center of the helical pattern. A pre-set spaced gap 305*g* is between every fourth adjacent coil of the body 305. The gaps 305*g* are configured such that as adjacent helical coils of the body 305 are compressed together substantially along the longitudinal axis $\ell$ (as illustrated in FIG. 3B), a diameter of the lumen 306 increases. Compressing the helical coils together, causes an inner diameter of the coils and a diameter of the lumen 306 to increase. Tensioning the body 305, e.g., pulling the coils apart causes the inner diameter of the coils and the diameter of the lumen 306 to decrease. A larger diameter lumen 306 may assist with reducing the tendency of the stent 300 to bind with the guidewire 320 and may assist with easing the stent's 300 ability to be translated along the guidewire 320. Various parameters of the helical coils of the body 305 may be adjusted, e.g., pitch, coil diameter, polymer diameter, number of windings, gap size, gap frequency, or the like, to adjust the reaction of the body 305 to tension and/or compression. Although the gaps 305*g* are illustrated between every fourth adjacent coil of the body 305, a gap 305*g* may be arranged along any point of the body 305 (e.g., between every coil, between every second, third, fifth, eighth, tenth coil, etc.). The coils are illustrated as strands attached to each other, e.g., beaded, polymer-coated, extruded, a combination thereof, or the like, forming a flat ribbon. A number of helical coils employed may be limited by parameters such as the pitch of the helical coils, etc. The stent 300 is illustrated in a deployed configuration in FIG. 3C with the guidewire 320 removed from the lumen 306, allowing the retention members 301, 302 to form. A first aperture 311 and a second aperture 312 each extend through a wall of the distal tube 303 into the lumen 306. A distal suture 321 extends along the stent 300 with a mid-portion 321*m* of the suture 321 extending through the first aperture 311 and the second aperture 312. A third aperture 313 extends through a wall of the proximal tube 304 into the lumen 306. A proximal suture 322 extends along the stent 300 with a mid-portion 321*m* of the suture 321 extending through the third aperture 313, through the lumen 306, and through a proximal end 300*p* of the stent 300. Ends 321*p* of the distal suture 321 are coupled to each other and ends 322*p* of the proximal suture 322 are coupled to each other such that a medical professional may manipulate the ends 321*p*, 322*p* (e.g., with the medical professional's finger(s) grabbing a loop created by the ends 321*p*, 322*p*, a handle of a device, or the like) by exerting tension or releasing tension on the sutures 321, 322. A delivery device 324, e.g., a pusher, about the guidewire 320 may assist with positioning the stent 300 and may provide a backstop proximal to the stent 300 during positioning or compressing of the stent 300 (e.g., pulling proximally on one or more of the sutures 321, 322 against the delivery device 324). For example, when the medical professional pulls the suture 321 proximally to position the stent 300, the delivery device 324 may not be used as a backstop because the delivery device may prevent the stent 300 from being translated proximally over the guidewire 320. The delivery device 324 may be used as a backstop to compress and/or elastically or plastically shorten the length of the stent 300, e.g., with coils of the body 305 being reinforced with an annealed (e.g., stainless steel) material such that body 305 maintains its shortened length.

In various embodiments, the stent 300 may be loaded onto a guidewire 320 and positioned within the body substantially similar to the methods described with reference to the stent 200 and suture 221 above. To lengthen the body 305 (e.g., within the ureter) the guidewire 320 may be proximally withdrawn to the proximal retention member 302 and the proximal suture 322 may be proximally pulled to also proximally pull the proximal retention member 302 into the bladder (while the distal retention member 301 retains its deployed form, anchored in the kidney) allowing the body 305 to extend (i.e., stretch) to a desirable length along the ureter and possibly into the bladder. While one hand holds the proximal suture 322, extending the body 305, and the same hand also holding the pusher 302 abutting the proximal end 300p, the second hand may withdraw the guidewire 320 from the lumen 306, allowing the proximal retention member 302 to form in the bladder. Alternatively, the guidewire 320 may be removed from the proximal pigtail 302 before extending the body 305 with the suture proximal suture 322. The second suture 322 may be used to make final adjustments in positioning the stent 300 by pulling the proximal suture 322 proximally. The proximal suture 322 may be released and removed from the stent 300 or may be left behind (e.g., taped externally to the thigh or left within the bladder) for later stent retrieval. The proximal suture 322 may be proximally pulled to substantially straighten out the proximal retention member 302 for removing the stent 300 because the distal retention member 301 is anchoring the remainder of the stent 300 while the proximal retention member 302 is straightened. The mid portion 322m of the proximal suture 322 within the lumen 306 may assist in guiding the proximal suture 322 proximally out of the stent 300 when desired.

In various embodiments, a medical professional may use one or more sutures and/or a delivery device to deliver, deploy, position, reposition, or withdraw the stent. For example, during delivery the medical professional may pull on a distal suture to compress a body with and against (or without) a delivery device (e.g., a pusher, a cannula, a catheter, a sheath, or the like), or the medical professional may pull on a proximal suture to extend the coil body. During translation of a stent over a guidewire, the guidewire may create friction within a lumen of the stent such that a portion of the body is tensioned (e.g., stretched from binding with the guidewire), and coils of the body are separated from each other such that a diameter of the lumen of the stent decreases. The medical professional may reduce the effects of guidewire friction by longitudinally compressing the body during stent translation. For example, the body may be compressed during delivery by the medical professional pulling a distal suture proximally such that the stent proximally abuts a delivery device (compressing the body) to translate the stent over a guidewire. Additionally, or in the alternative, the medical professional may orient or re-orient a position of the stent, e.g., a distal retention member, by torqueing the body in a direction counter to the direction of the coils (e.g., coils wound in a clockwise helix may be turned in a counter-clockwise direction such that a diameter of a lumen within the coils is substantially maintained). This direction may be marked on a proximal portion of the stent and the torsional force may be transferred to the stent by the medical professional's hand directly to the stent or through a guidewire, a cannula, a pusher, a sheath, or a connected handle. The medical professional may also use a suture residing within and/or outside of a patient to remove the stent from the patient. For example, a professional may leave the proximal end or ends of a suture inside the patient's body or just outside of the body. A suture coupled with a proximal end of the stent may be pulled proximally to straighten the proximal retention member in the bladder such that it may be proximally translated through the urethra. As the proximal retention member is translated through the urethra, the distal retention member may be straightened by the stent being translated through the ureter. However, other means and steps to remove stents in coordination with a distal suture (with or without a proximal suture), guidewire, and pusher or other delivery device, are contemplated. A suture may be non-absorbable, absorbable, dissolvable, or biodegradable. A suture may be a monofilament, braided, and may contain a hydrophilic coating or the like. A length of a suture from a mid-portion to the coupled proximal extending ends may be about 45 cm. Sutures may be different colors or include visual markers such that they may be identified from each other. A suture may be sleeved or coated such that it does not entangle with other sutures or devices.

In various embodiments, a distal tube or a proximal tube may include one or more apertures configured for a distal suture or a proximal suture that are arranged differently than those discussed above, e.g., differently than the apertures 211, 212, 311, 312 of FIGS. 2A-3C. A distal tube and/or proximal tube of one embodiment of a stent described here may alternatively or additionally include apertures of another embodiment of a stent.

Figure 4:
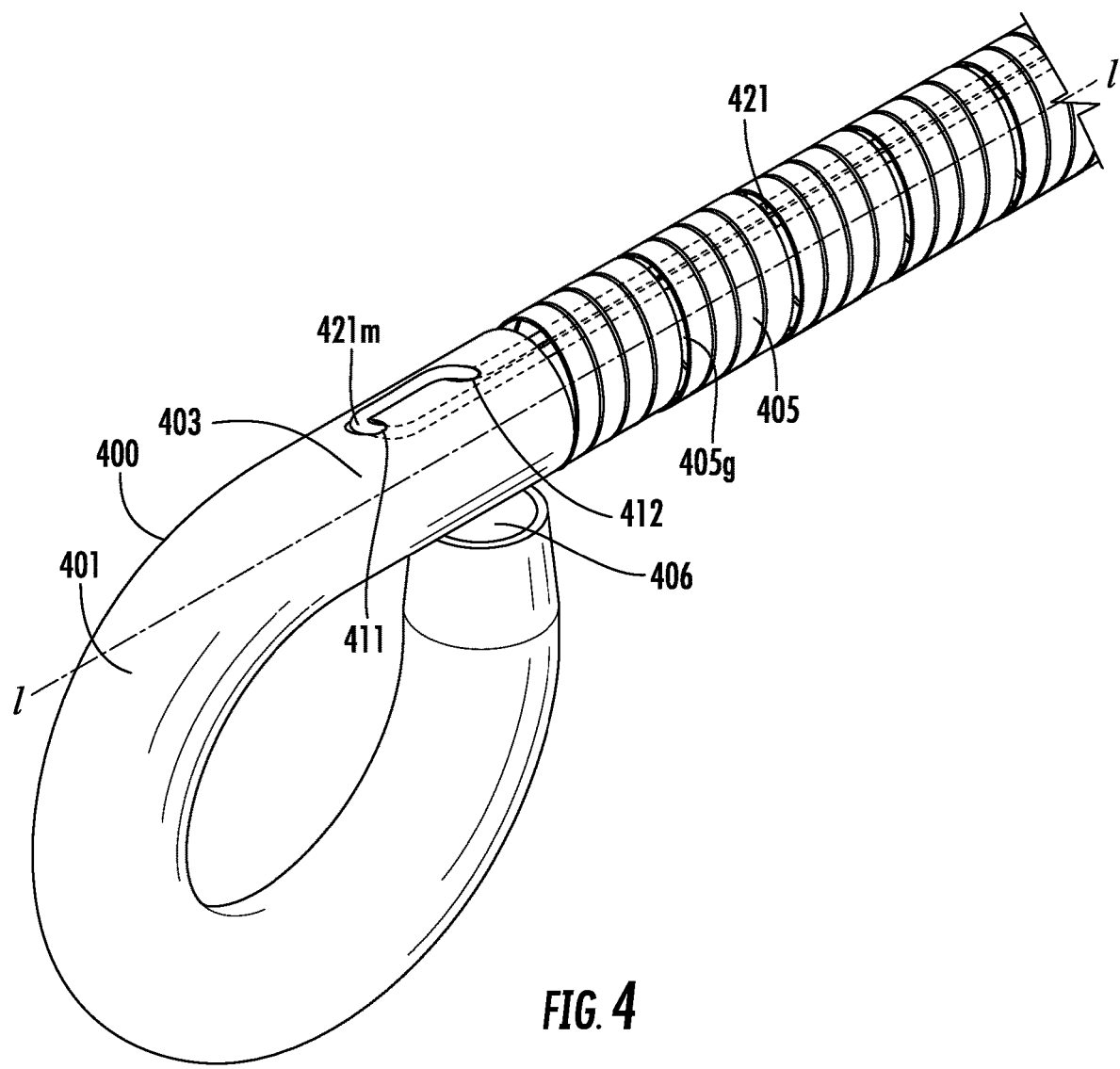
FIG. 4 illustrates a distal portion of a stent, in accordance with an embodiment of the present disclosure.

With reference to FIG. 4, a distal portion of a stent 400 according to an embodiment of the present disclosure is illustrated in a deployed configuration. The stent 400 has a body 405, a distal tube 403 extending from the body 405, and a distal retention member 401 extending from the distal tube 403. The distal tube 403 includes a first aperture 411 and a second aperture 412 extending through a wall of the distal tube 403 into a lumen 406 such that the first aperture 411 and the second aperture 412 are aligned parallel to a longitudinal axis $\ell$. A mid-portion 421m of the distal suture 421 extends through the first and second apertures 411, 412. The distal suture 421 extends through the lumen 406 of the stent 400 with only the mid portion 421m extending outside of the stent 400 along an outer surface of the wall of the distal tube 403. A length of the distal suture 421 along the stent 400 is entirely within the lumen 406 except for the mid portion 421m, reducing a chance of the distal suture 421 contacting other devices or anatomy compared to a distal suture 421 that does not have a length of the distal suture 421 along the stent 400 within the lumen 406. The distal suture 421 does not intersect the longitudinal axis $\ell$, reducing the chance of the distal suture 421 contacting with a guidewire within the lumen 406 compared to a distal suture 421 that does intersect the longitudinal axis $\ell$.

Figure 5:
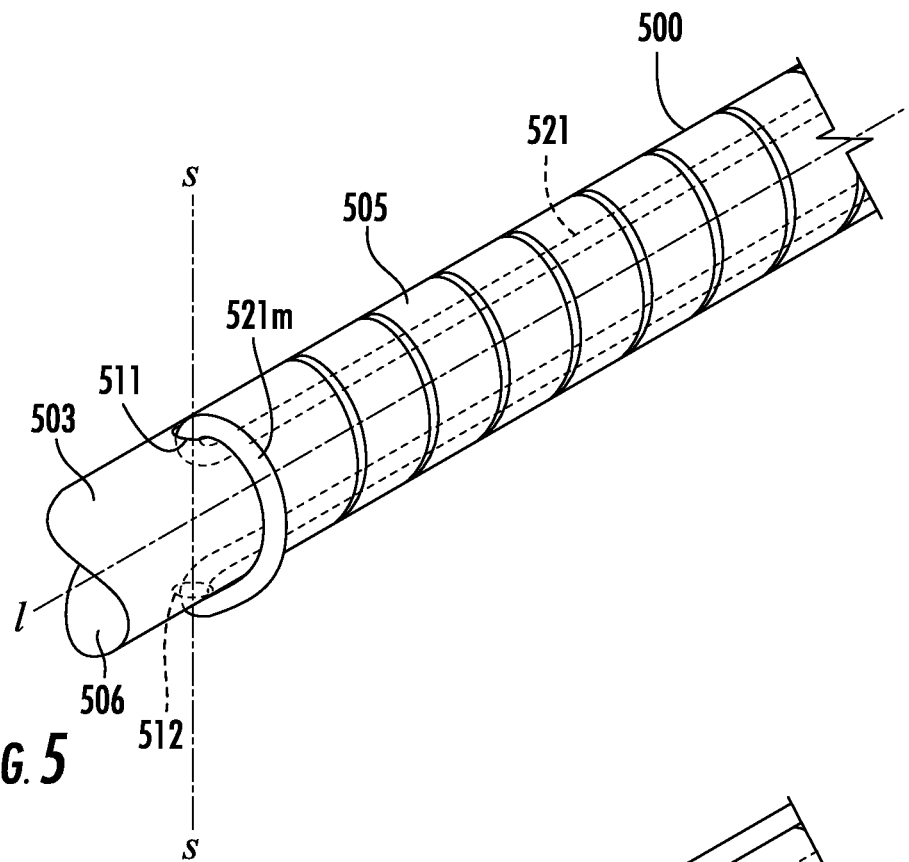
FIG. 5 illustrates a portion of a stent, in accordance with an embodiment of the present disclosure.

Referring to FIG. 5, a distal portion of a stent 500 according to an embodiment of the present disclosure is illustrated. The stent 500 has a body 505 and a distal tube 503 extending from the body 505. The distal tube 503 includes a first aperture 511 and a second aperture 512 extending through a wall of the distal tube 503 into a lumen 506 of the stent 500. The first aperture 511 and the second aperture 512 are aligned forming a suture axis $\delta$ that intersects a longitudinal axis $\ell$ of the stent 500. A mid-portion 521m of the distal suture 521 extends through apertures 511, 512 such that the distal suture 521 extends within the lumen 506 along the wall of the distal tube 503, through the first aperture 511, along an outside surface of the wall of the distal tube 503, through the second aperture 512 into the lumen 506, and along the wall of the distal tube 503 within the lumen 506. A length of the distal suture 521 along the stent 500 is entirely within the lumen 506 except for the mid portion 521m, reducing a chance of the distal suture 521 contacting other devices or anatomy outside of the lumen 506 compared to a distal suture 521 that does not have a length of the distal suture 521 along the stent 500 within the lumen 506. The distal suture 521 does not intersect the longitudinal axis $\ell$, reducing the chance of the distal suture 521 contacting a guidewire within the lumen 506 compared to a distal suture 521 that does intersect the longitudinal axis ℓ.

Figure 6:
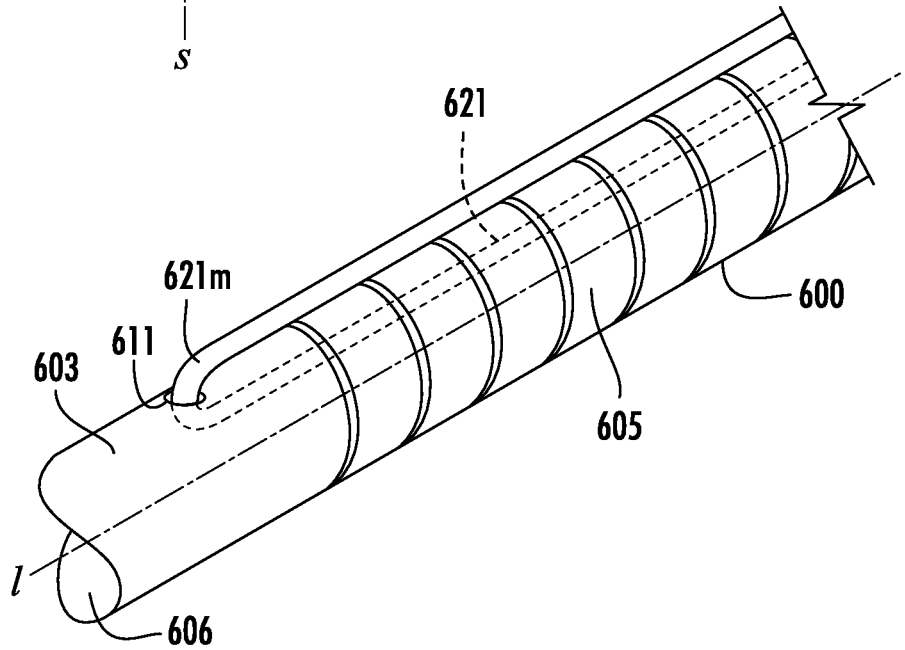
FIG. 6 illustrates a portion of a stent, in accordance with an embodiment of the present disclosure.

Referring to FIG. 6, a distal portion of a stent 600 according to an embodiment of the present disclosure is illustrated. The stent 600 has a body 605 and a distal tube 603 extending from the body 605. The distal tube 603 includes an aperture 611 extending through a wall of the distal tube 603 into a lumen 606 of the stent 600. A mid-portion 621m of the distal suture 621 extends through the aperture 611 such that the distal suture 621 extends along the outer surface of the wall of the distal tube 603 and along the lumen 606. The distal suture 621 does not intersect the longitudinal axis ℓ, reducing the chance of the distal suture 621 contacting a guidewire within the lumen 606 compared to a distal suture 621 that does intersect the longitudinal axis ℓ.

Referring to FIGS. 7A and 7B, a stent 700 according to an embodiment of the present disclosure is illustrated. In FIG. 7A, the stent 700 is in a delivery configuration arranged over a guidewire 720 extending through a lumen 706 of the stent 700, thereby substantially straightening a distal retention member 701 and a proximal retention member 702, each extending from a distal tube 703 and a proximal tube 704, respectfully. The stent 700 includes a body 705 wound in coils in a helical pattern about a longitudinal axis ℓ of the stent 700. The body 705 defines a lumen 706 along the longitudinal axis ℓ through the helical pattern. The stent 700 is illustrated in a deployed configuration in FIG. 7B with the guidewire 720 removed from the lumen 706, allowing the retention members 701, 702 to form. A first aperture 711 and a second aperture 712 each extend through a wall of the distal tube 703 into the lumen 706. A suture 721 extends along the stent 700 with a mid-portion 721m of the suture 721 extending through the first aperture 711 and the second aperture 712. An adhesive 716 (e.g., a heat shrink tube, glue, a melted material, or the like) may be disposed about a portion of the suture 721 and the proximal tube 704, fixing the suture 721 along the stent 700 proximal to the body for manipulation. Ends 721p of the distal suture 721 are coupled to each other such that a medical professional may manipulate the ends 721p (e.g., with the medical professional's hand, a handle of a device, or the like) by exerting tension or releasing tension on the suture 721. Because the adhesive 716 fixes the suture 721 to the proximal tube 704, a length 723 of the suture 721 between the adhesive 716 and the apertures 711, 712 limits an amount of extension of the body 705. The length 723 may be adjusted to limit extension of the coil body 705 to extend such that the body 705 does not make substantial contact with the guidewire 720. A delivery device 724 about the guidewire 720 proximal to the stent 700 may assist with positioning the stent 700 and may provide a proximal backstop during positioning or compressing of the stent 700 (e.g., pulling proximally on the suture 721 against the delivery device 724).

Referring to FIG. 8, a stent 800 according to an embodiment of the present disclosure is illustrated in a delivery configuration over a guidewire 820. The stent 800 has a first aperture 811 through a wall of a distal tube 803 and a second aperture 812 through a wall of a proximal tube 804 that is offset about 180° about a longitudinal axis ℓ of the stent 800. A mid-portion 821m of a distal suture 821 extends through the first aperture 811 and a proximal a mid-portion 822m of a proximal suture 822 extends through the second aperture 812. The offset apertures 811, 812 allow the distal and proximal sutures 821, 822 to be separately arranged within a lumen 806 of the stent 800 such that they do not contact each other and possibly become entangled. The distal suture 821 may be used to proximally translate the stent 800 or compress the body of the stent 800. The proximal suture 821 may be used to proximally translate the stent 800, extend the body of the stent, or retrieve the stent 800.

Referring to FIG. 9, a stent 900 according to an embodiment of the present disclosure is illustrated in a delivery configuration over a guidewire 920. The stent 900 has an aperture 911 through a wall of a distal tube 903 into a lumen 906 of the stent 900. A mid-portion 921m of a suture 921 extends through the aperture 911. An inner diameter of the lumen 906 may be a variety of French sizes, e.g., 4, 5, 6, 7, 8 French, or the like. The lumen 906 of, e.g., 4 or 5 French stent 900, is slightly larger than the outer diameter of the guidewire 920 such that a tensioned body 905 may cause the coils of the body 305 to deflect to a small enough diameter such that the diameter of the lumen 906 decreases to bind the stent 900 to the guidewire 920. Due to the shape-memory of the retention members, the lumen 906 within the retention members has a frictional or interference fit with the guidewire 920. A medical professional may use the guidewire 920 to extend a length of a body 905 of the stent 900. For example, the medical professional may position the distal end of the guidewire 920 within the lumen 906 of the proximal retention member using a delivery device 924 as a backstop, because the stent 900 and the guidewire 920 have a frictional or interference fit with the retention member(s), a medical professional may translate the guidewire 920 proximally to cause the coils of the body 905 to separate from each other, extending the length of the body 905 with the distal retention member formed in the kidney to resist the proximal translation of the guidewire 920. The guidewire 920 may be removed from the lumen 906 by using the delivery device 924 as a backstop. In some embodiments, a length of the body 905 may adjust to the length of the ureter with the formed retention members substantially maintaining the length.

The stent 900 and pusher 924 may be loaded onto the guidewire 920 externally to the body of the patient by substantially straightening the distal retention member and back-loading it onto the proximal end of the guidewire 920. The stent 900 may be pushed distally (i.e., rather than pulled) onto the guidewire 920 to minimize the stent 900 from binding to the guidewire 920. One hand may push the stent 900 and a second hand may be used to steady the guidewire 920 distal to the stent 900 and/or to steady the guidewire 920 at its proximal end as the guidewire 920 exits the stent lumen 906. The distal end of pusher 924 may be loaded onto the proximal end of the guidewire 920 by pushing or pulling the pusher 924 distally until the distal end of the pusher 924 abuts the proximal end of the stent 900. The stent 900 may be distally translated by using one hand to grip the proximal end of the guidewire 920 and the other hand to distally translate the pusher 924 to advance the stent 900 into the patient and into the kidney. The pusher 924 compresses the body 905 to maintain or increase the stent lumen 906 inner diameter to decrease binding to the guidewire 920 as the distal retention member resists distal translation of the stent 900 because the distal retention member tends to partially form in its deployed or curved configuration out of alignment with the longitudinal axis ℓ such that it engages the guidewire 920. The stent 900 may be further positioned proximally with the distal retention member in the kidney. One hand may grip the proximal end of the guidewire 920 while the other hand proximally pulls on the suture 921, compressing the body 905 to maintain or increase the stent lumen 906 inner diameter as the proximal retention member resists proximal translation of the stent 900 because the proximal retention member tends to partially form into the deployed configuration out of alignment with the longitudinal axis $\ell$ such that it engages the guidewire 920. The stent 900 may be positioned along the guidewire 920 (e.g. within the kidney, ureter, and bladder) to a desired location. To deploy the distal retention member, the pusher 924 may be held stationary with one hand, abutting the proximal end of the stent 900, while the second hand proximally withdraws the guidewire 920 to allow the distal retention member to form. The formed distal retention member may be moved in the kidney by using the first hand to proximally pull the suture 921 and/or distally pushing the stent 900 with the pusher 924 over the guidewire 920 while holding the guidewire 920 with the second hand. Stent length sufficiency (e.g., in reference to the ureter length) may be checked via radiopaque markers in reference to one or more of the ureteral orifices, bladder, kidney, and ureter. The length of the body 905 may be axially extended to a desired length by releasing the pusher 924 and releasing or proximally pulling the guidewire 920 with the proximal retention member binding to the guidewire 920 as it tends to partially form into the deployed configuration out of alignment with the longitudinal axis $\ell$ such that it engages the guidewire 920. The body 905 may be extended to a desirable length. With the body 905 extended by the guidewire 920, the pusher 924 may be held abutting the proximal end of the stent 900. The guidewire 920 may be proximally withdrawn, causing the body 905, bound to the guidewire 920 to compress, assisting with releasing the guidewire 920 from the lumen 906, allowing the proximal retention member to form in the bladder.

Figure 10A:
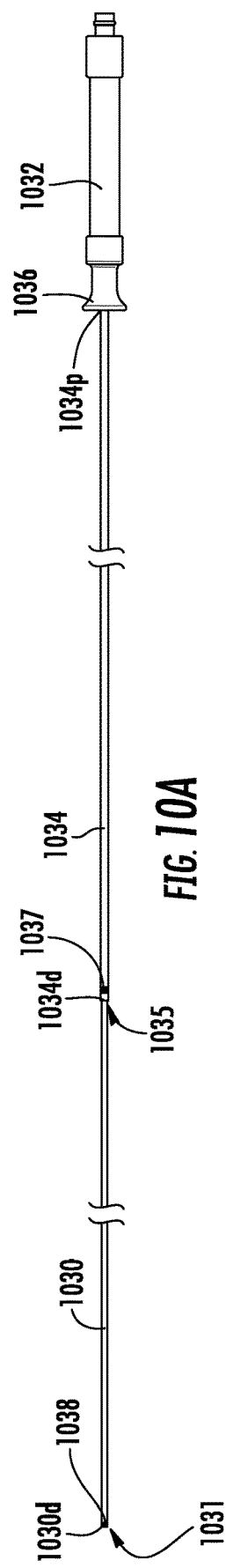
FIG. 10A illustrates a stent delivery device, in accordance with an embodiment of the present disclosure.
Figure 10B:
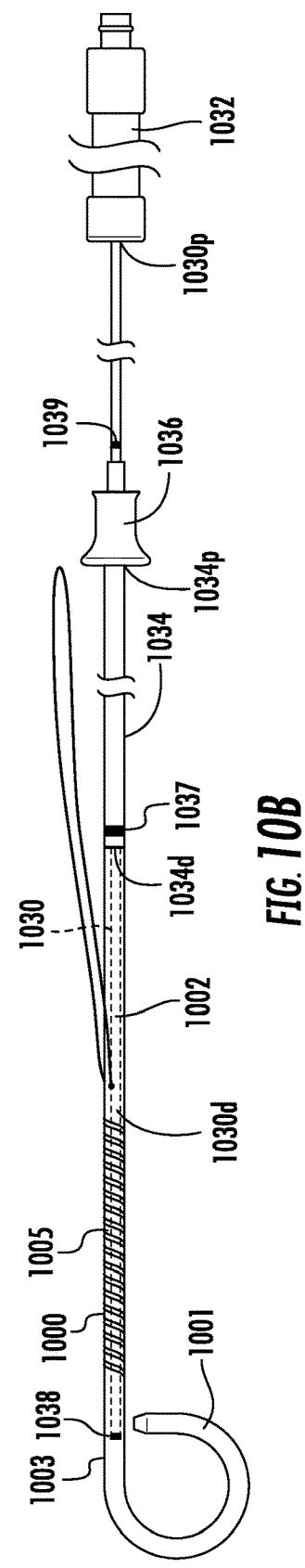
FIG. 10B illustrates the stent delivery device of FIG. 10A with a stent for deployment, in accordance with an embodiment of the present disclosure.

Referring to FIGS. 10A and 10B, a stent delivery device according to an embodiment of the present disclosure is illustrated, which includes a cannula 1030 having a proximal end 1030p, a distal end 1030d, and a cannula lumen 1031 therethrough. A handle 1032 is attached at the proximal end 1030p of the cannula 1030. A pusher 1034 is disposed over the cannula 1030. The pusher 1034 has a proximal end 1034p, a distal end 1034d, and a pusher lumen 1035 therethrough. A knob 1036 is attached to the proximal end 1034p of the pusher 1034. The knob 1036 is reversibly coupled to the handle 1032 and may be lockable to prevent premature deployment of a stent. The cannula lumen 1031 is configured to accept a guidewire. In FIG. 10B, a stent 1000 is disposed over the cannula 1030. The pusher 1034 has an outer diameter the same or substantially the same length as an outer diameter of the stent 1000. The cannula 1030 may provide protection from frictional forces between the guidewire and the stent 1000 such that the guidewire does not contact a portion of the stent 1000 that is on the cannula 1030. The stent 1000 is in a partially deployed configuration or a loading configuration where the distal retention member 1001 may be prepared to be backloaded over a guidewire to be straightened before delivery. The distal retention member 1001 of the stent is formed and a proximal retention member 1002 is straightened by the cannula 1030 and the guidewire within the stent 1000 (but proximal to the distal retention member 1001) such that the distal end 1030d of the cannula 1030 is between the distal retention member 1001 and the body 1005. The stent 1000 may be deployed by unlocking the locking knob 1036 from the handle 1032 and translating the handle 1032 and the cannula 1030 proximally with respect to the locking knob 1036 and the pusher 1034. This motion abuts the distal end 1034d of the pusher 1034 against the stent 1000 such that the cannula 1030 may be removed from the stent 1000. The distal end 1034d of the pusher 1034 has a first radiopaque band 1037 that may be visualized using, e.g. fluoroscopy, during operation of the stent delivery device and may be visually referenced, e.g., to indicate a proximal end of the stent 1000 abutting the pusher 1034. The cannula 1030 includes a second radiopaque band 1038 at the distal end 1030d and a third radiopaque band 1039 proximal to the second radiopaque band 1038. The second and third radiopaque bands 1038, 1039 may be spaced apart from each other such that when the third radiopaque band 1039 is proximally withdrawn from the locking knob 1036, the second radiopaque band 1038 is positioned within a distal tube 1003 indicating that the distal retention member 1001 has formed. Additionally, for example, the radiopaque bands 1037, 1038, 1039 may be visualized with reference to each other to indicate a length of the stent 1000 that has not yet been deployed (e.g., the distance between the second radiopaque band 1038 and the first radiopaque band 1037).

In various embodiments, one or more radiopaque markers may be disposed on a stent, a cannula, a pusher, a sheath, and/or the like. The markers may be bands or other shapes that may be identifiable under fluoroscopy. The markers may be arranged at a measured distance from each other such that anatomies and/or devices may be measured in relation to the markers. One or more markers may be located at an end of a component of a device. One or more markers may be disposed at a location of a device that indicates when a portion of a stent is deployed. For example, a marker may be placed on a cannula such that when the marker is proximally withdrawn and visualized external to the body or is visualized in relation to another marker, this visualization indicates to a medical professional that a distal retention member has been deployed.

Figure 11:
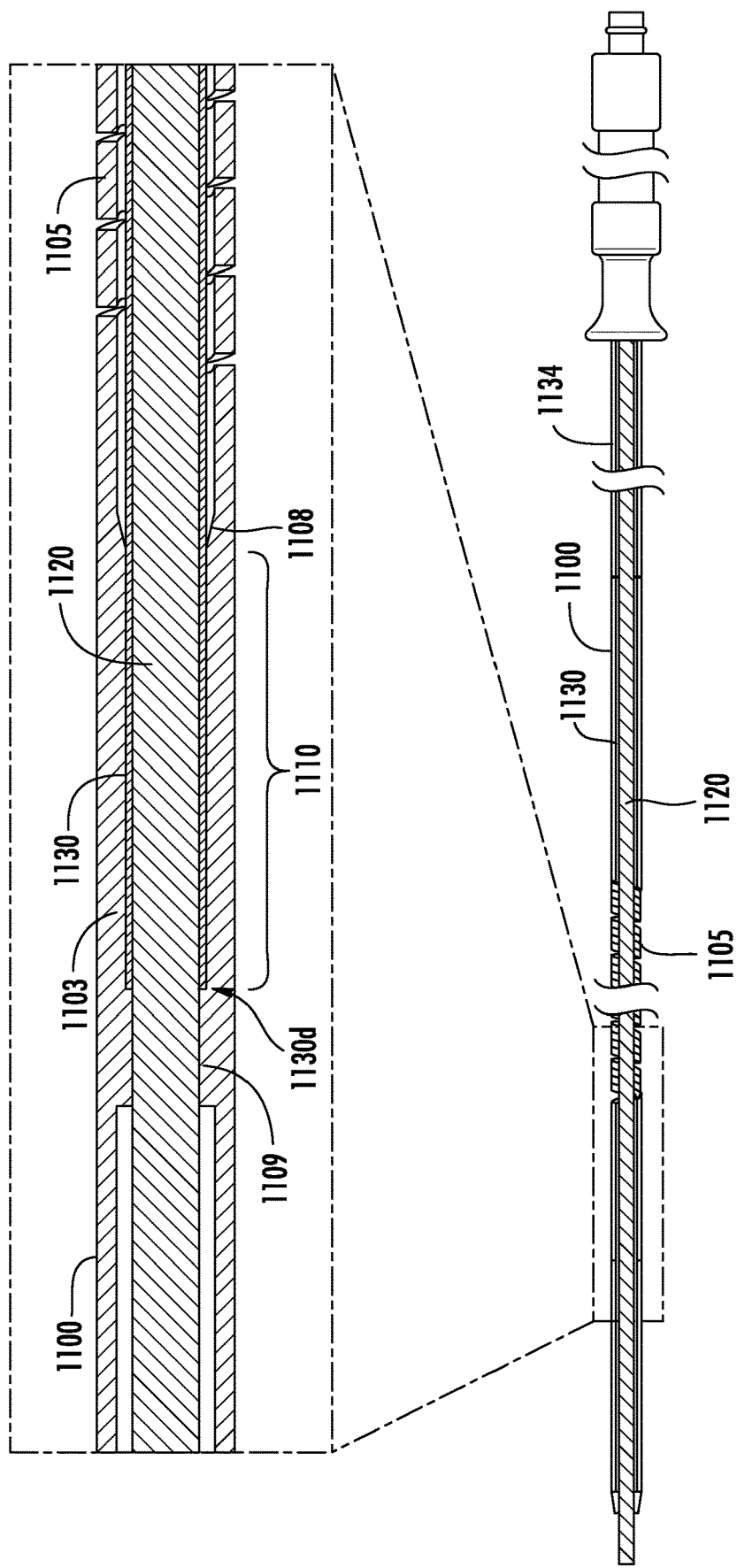
FIG. 11 illustrates a stent system with a stent in a delivery configuration, in accordance with an embodiment of the present disclosure.

Referring to FIG. 11, a stent delivery system according to an embodiment of the present disclosure is illustrated, which includes a delivery device having a cannula 1130 and a pusher 1134 disposed over the cannula 1130. A guidewire 1120 is extended within a lumen of the cannula 1130. A stent 1100 is disposed over the cannula 1130 in a delivery configuration. The stent 1100 includes an engagement portion 1110 along a wall of the stent 1100 at a distal tube 1103 having an inner diameter that is about the same size as an outer diameter of the cannula 1130. The cannula 1130 is frictionally engaged with the engagement portion 1110 of the stent 1100 such that the cannula 1130 may be translated proximally and distally to also translate the stent 100 proximally and distally. The stent includes a taper 1108 along the wall of the stent 1100 defining a distally decreasing inner diameter of the stent 1100 such that the cannula 1130 may be guided from a larger inner diameter of the stent 1100 proximal to the engagement portion 1110 into the smaller inner diameter of the engagement portion 1110. The stent 1100 includes a ring portion 1109 disposed within the wall of the stent 1100. The ring portion 1109 has an inner diameter that is smaller than the outer diameter of the cannula 1130. The ring portion 1109 may abut a distal end 1130d of the cannula 1130 when the cannula 1130 is extended within the engagement portion 1110. The ring portion 1109 may prevent further distal translation of the cannula 1130 past the engagement portion 1110. The ring portion 1109 also provides a surface for the cannula 1130 to distally translate the stent 1100, when applying an axial force to translate the stent 1100 at a location distal to the body 1105, rather than within or proximal to the body 1105, which may cause buckling of the body 1105 during delivery. The cannula 1130 and/or guidewire 1120 may be withdrawn from the stent 1100, e.g., for deployment, by abutting the pusher 1134 against a proximal end of the stent 1100 and translating the cannula and/or guidewire 1120 proximally with respect to the pusher 1134.

A stent delivery system, e.g. as illustrated in FIG. 11, may be assembled with the pusher 1134 releasably locked to the cannula 1130 via a handle. The stent 1100 may be loaded onto the cannula 1130 by substantially straightening the proximal retention member and inserting the cannula 1130 through the lumen of the stent 1100. The proximal end of the stent 1100 may be slid over the distal end 1130d of the cannula 1130 (which may be angularly cut forming a smaller distal tip outer diameter extending proximally to a larger outer diameter of the cannula 1130) by proximally pushing (i.e., not pulling) the stent 1100 onto the cannula 1130, until the cannula 1130 engages a smaller inner diameter of an engagement portion 1110 and may abut a ring portion 1109 of the stent 1100. The proximal end of the stent 1100 may abut the pusher 1134. The guidewire 1120 may be placed into the kidney using fluoroscopy (if not already placed in a previous procedure, e.g., flexible ureteroscopy, or the like). To load the assembled stent 1100 and delivery device onto the guidewire 1120, the distal retention member may be substantially straightened and back-loaded onto the proximal end of the guidewire 1120 and distally pushed using the handle or the releasably locked pusher 1134. To prevent the stent 1100 from disengaging from the cannula 1130, which may result in undesirable stretching, or damage, the pusher 1134 may be locked. One hand of a medical professional may push the stent 1100 via the pusher 1134 or handle while the second hand steadies the guidewire 1120 distal to the stent 1100 and then to steady a proximal end of the guidewire 1120 exiting a lumen of the cannula 130 at the medical luer hub at a proximal end of the cannula 1130. To advance the stent 1100 distally, one hand may grip the proximal end of the guidewire 1120 and the second hand may advance the locked pusher 1134 to distally advance the stent 1100 into the kidney over the guidewire 1120. The stent 1100 is at least partially supported by the cannula 1130. The cannula 1130 is releasably engaged with the stent 1100 at the engagement portion 11110. The pusher 1134 is abutting the proximal end of the stent 1100, minimizing the stent 1100 from undesirably extending as the stent 1100 is moved along the guidewire 1120. Friction between tissue (e.g., the ureter) and the stent 1100 during distal translation may cause the body 1105 to axially compress to maintain or increase the inner diameter of the stent 1100 (decreasing binding of the body 1105) as the distal retention member resists distal translation against the guidewire 1120 as the member tends to partially form into the deployed configuration. To position the distal retention member in the kidney, the stent 1100 may need to be translated proximally. This may be accomplished by one hand steadying the proximal end of the guidewire 1120 while the second hand proximally pulls the pusher 1134 and cannula 1130. When proximally pulling the stent 1100 along the guidewire 1120 with the cannula end 1130d still engaging the engagement portion 1110, the friction between tissue (e.g., the ureter) and the stent 1100 during proximal translation may cause the body 1105 to axially compress to maintain or increase the stent lumen inner diameter to decrease stent 1100 binding as the cannula 1130 engagement with the engagement portion 1110 is maintained. The distal retention member may be adjusted over the guidewire 1120 as desired. Once a desirable position of the distal retention member is accomplished, the handle may be held with one hand as the second hand moves the guidewire 1120 by gripping the proximal end and proximally translating the guidewire 1120 to allow the distal retention member to form. During (or after) deployment of the distal retention member, the handle may be rotated about its longitudinal axis (possibly under fluoroscopy) for reorientation of the distal retention member, e.g., in the kidney. The guidewire 1120 may be removed from the cannula 1130 to allow a supply of contrast, e.g., into the kidney, via a path through the medical luer hub, through the cannula 1130, through coils of the body 1105, and out of distal end of the stent 1100 for fluoroscopic imaging of the kidney. The stent 1100 may be moved by using the first hand to proximally pull the handle or distally pushing the handle over the guidewire 1120, while holding and steadying the proximal end of the guidewire 1120 with the second hand (if the guidewire 1120 is not removed). The memory set curvature of the proximal retention member, or the body 1105 in axial tension, may bind the stent 1100 to the distal end 1130d of the cannula 1130 such that proximally pulling the handle may extend the body 1105 and may proximally pull the proximal retention member into the bladder. Once a desirable stent 1100 length is achieved, the first hand may hold the handle with the pusher 1134 tip abutting the proximal end of the stent 1100. The guidewire 1120 may be removed from the cannula 1130 lumen (if not removed already). The locking knob of the pusher 1134 may be released from the handle of the cannula 1130 with the second hand and held stationary. The first hand may proximally move the handle, causing the cannula 1130 and the engagement portion 1110 of the stent 1100 to proximally translate, compressing the body 1105 to an increased column strength where further proximal translation axially forces the cannula end 1130d to release from the engagement portion 1110. With the cannula 1130 disengaged from the engagement portion 1110, the cannula 1130 may be proximally withdrawn from the stent 1100. With the cannula 1130 and guidewire 1120 removed from the stent 1100, a proximal suture (like that of FIG. 10B or another embodiment described herein) may be used to proximally pull the proximal end of the stent 1100. The proximal suture may reside in the in the bladder and partially within the ureter. Proximally pulling the proximal suture may extend the body 1105 and may proximally pull the proximal retention member into or already within the bladder to be formed to the deployed configuration. With the cannula 1130 within the stent 1100 lumen, near the proximal end of the body 1105, or solely in the proximal retention member, the proximal suture or the cannula 1130 may be used to proximally pull the proximal end of the stent 1100 within the bladder.

Figure 12:
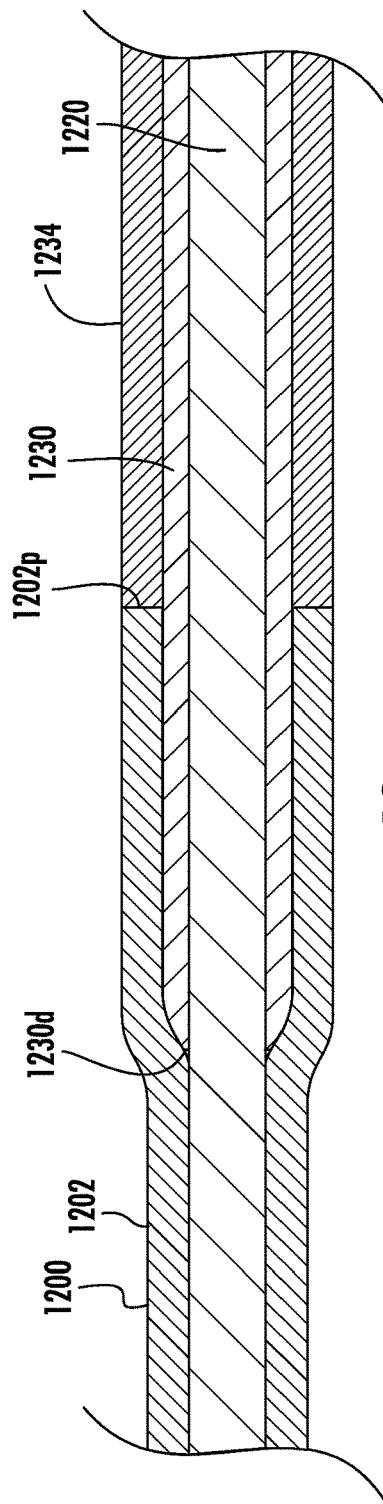
FIG. 12 illustrates a stent system with a stent in a delivery configuration, in accordance with an embodiment of the present disclosure.

Referring to FIG. 12, a stent delivery system according to an embodiment of the present disclosure is illustrated, which includes a delivery device having a cannula 1230 and a pusher 1234 disposed over the cannula 1230. A guidewire 1220 is extended within a lumen of the cannula 1230. A portion of a proximal retention member 1202 of a stent 1200 is disposed over the cannula 1230 in a delivery configuration. The portion of the proximal retention member 1202 disposed over the cannula 1230 may be, e.g., about 6 mm in length, about 1 mm to about 10 mm in length, etc. The cannula 1230 has an outer diameter larger than an inner diameter of the stent 1200 to create a friction or interference fit between the distal end of the cannula and proximal end of the stent. The distal end 1230d of the cannula 1230 has a distally decreasing outer diameter such that the stent 1130 may be guided onto the distal end 1230d of the cannula 1230 from the smaller outer diameter of the distal end 1230d to the larger outer diameter of the remainder of the cannula 1230. In the delivery configuration, the stent 1200 may be translated proximally or distally by translating the cannula 1230 proximally or distally with the cannula 1230 engaged with the proximal retention member 1202. The stent 1200 may be deployed by translating the proximal retention member 1202 distally off of the cannula 1230 by unlocking and translating the pusher 1234 distally with respect to the cannula 1230.

A stent delivery system, e.g. as illustrated in FIG. 12, may be assembled with the pusher 1234 releasably locked by a knob to a handle. The knob may have a limited travel distance when unlocked from the handle, e.g., about 10 mm. The stent 1200 may be loaded by substantially straightening the proximal retention member 1202 and placing the stent 1200 over the distal end 1230d of the cannula 1230 until the proximal end of the stent 1202p abuts the distal end of the pusher 1234. The guidewire 1220 may be distally translated into the kidney (if it is not already positioned from a previous procedure, e.g., flexible ureteroscopy). To load the delivery system onto the guidewire 1220, the distal retention member may be substantially straightened and back-loaded onto the proximal end of the guidewire 1120. The stent 1200 may be distally pushed further onto the guidewire 1220 (i.e., pulled to avoid binding and possible disengagement of the stent 1200 off of the cannula 1230). The proximal end of the guidewire 1220 may be directed into a lumen of the cannula 1230 with one hand distally pushing the stent 1200 via the pusher 1234 or handle. The second hand may be used to steady the guidewire 1220 initially distal to the stent 1200 and then to steady the proximal end of the guidewire 1200 to proximally exit the cannula 1230, e.g., at a medical luer hub of the handle. The stent 1200 may be distally translated by one hand gripping the proximal end of the guidewire 1220 and the second hand distally advancing the pusher 1234. Friction between body tissue (e.g., the ureter) and the stent 1200 during distal translation may axially compress the body 1205 to a column strength that maintains or increase an inner diameter of a lumen of the stent 1200 to decrease binding as the distal retention member and the proximal retention member 1202 resist distal translation against the guidewire 1220 as the retention members tend to partially form into the deployed configuration out of alignment with the longitudinal axis $\ell$. The distal retention member may be deployed by distally advancing the distal retention member into the kidney. Once the medical professional is satisfied with the initial placement of the distal retention member, the handle (and pusher 1234) may be held with one hand such that the pusher 1234 abuts the proximal end 1202p of the stent as the second hand proximally translates the guidewire 1220 by gripping the proximal end of the guidewire 1220 to allow the distal retention member to form. During (or after) the deployment of the distal retention member, the handle may be rotated for torque transmission about its longitudinal axis to orient the distal retention member in the kidney. Torque transmission may be applied to the stent 1200 in a direction opposite of the windings of the body of the stent 1200 (e.g., clockwise torque for a counter-clockwise body). The direction of a preferred rotation may be marked on the handle or pusher 1234. The deployed distal retention member may be moved within the kidney, while the guidewire 1220 resides in the body of the stent 1200 to support the column strength of the stent 1200, and by distally pushing the handle while the other hand grips the proximal end of the guidewire 1220. The guidewire 1220 may be proximally withdrawn from the cannula 1230 to allow additional space for a supply of contrast, e.g., along the stent and into the kidney and ureter via the medical luer hub for fluoroscopic imaging of the kidney and ureter. Removing the guidewire 1220 may alleviate a concern of the body of the stent 1200 binding to the guidewire 1220. The stent 1200 may be moved to a desirable position without the guidewire 1220 by proximally pulling the handle as the cannula 1230 is engaged with the proximal end 1202p of the stent 1200. Under fluoroscopy, the length of the stent 1200 may be observed with reference to the length of the ureter, kidney, bladder and various radiopaque markers along the cannula 1230, pusher 1234, and/or stent 1200. The stent 1200 length may be adjusted by proximally pulling the handle while monitoring the distal retention member anchored within the kidney. The stent 1200 may be repositioned and the body may be extended to a desired length and position. When a desirable position and length is achieved, the first hand may hold the handle of the cannula 1230, manipulating the locked knob of the pusher 1234 to unlock and distally translate the knob (e.g., with the thumb) to distally translate the pusher 1234 to abut the proximal end 1202p of the stent and distally push the stent 1200 off of the cannula 1230 such that it is no longer engaged with the cannula 1230.

Figure 13:
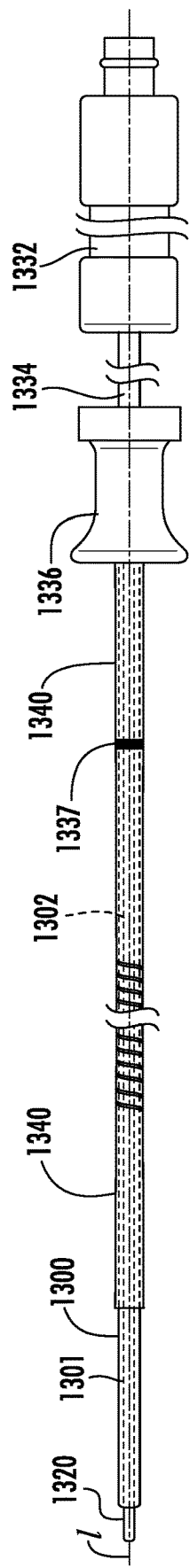
FIG. 13 illustrates a stent system, with a stent in a delivery configuration in accordance with an embodiment of the present disclosure.

Referring to FIG. 13, a stent delivery system according to an embodiment of the present disclosure is illustrated, which includes a stent 1300 in a delivery configuration over a guidewire 1320 with the retention members 1301, 1302 straightened. A sheath 1340 is extended over the stent 1300. In the delivery configuration, the shape-memory of the retention members 1301, 1302 are partially formed such that they are not parallel with a longitudinal axis $\ell$ of the stent 1300. This partial formation of the retention members 1301, 1302 enact a degree of radial force onto an inner surface of the sheath 1340, coupling the stent 1300 to the sheath 1340. Because the stent 1300 is slidably coupled with in the sheath 1340, the stent 1300 may be translated over the guidewire 1320 by translating the sheath 1340. The sheath 1340 may be translated by manipulating a knob 1336 attached to a proximal end of the sheath 1340. A pusher 1334 having an outer diameter substantially matching an outer diameter of the stent 1300 is extended over the guidewire 1320 proximal to the stent 1300. The pusher includes a radiopaque band 1337 that may be visualized, e.g., via fluoroscopy for locating the proximal end of the stent 1300 and/or the distal end of the pusher 1337. The pusher 1334 may be used to deploy the stent 1300 from the sheath 1340 and/or the guidewire 1320. For example, the pusher 1334 may abut the proximal end of the stent 1300 and the sheath 1340 may be translated proximally with respect to the pusher 1334 such that the stent 1300 is forced out of the sheath 1340 by the pusher 1334 acting as a proximal backstop. The pusher 1334 may be translated by manipulating a handle 1332 attached to a proximal end of the pusher 1334.

A stent delivery system, e.g. as illustrated in FIG. 13, may be assembled by back-loading the stent delivery device and stent 1300 onto a guidewire 1320 and distally pushing the system into the kidney. The tendency of the proximal retention member 1302 to partially form binds the stent 1300 to the inside of the sheath 1340, allowing the stent 1300 to be translated by translating the sheath 1340 or pusher 1334. The guidewire may be proximally withdrawn to allow the distal retention member 1301 to form. The formed distal retention member 1301 may also be translated along the guidewire 1320 by translating the stent 1300. A length of the stent 1300 may be checked within the patient. The knob 1336 may be unlocked and the sheath 1340 may be proximally withdrawn while the handle 1332 and pusher 1334 are held stationary to abut to the proximal end of the stent 1300 to deliver the stent 1300 within the ureter. A length of the stent 1300 may be adjusted (e.g., the body and/or retention members 1301, 1302) by proximally pulling the sheath 1340 and pusher 1334 simultaneously as the proximal retention member 1302 is bound to the sheath 1340. The extended body may be released by proximally pulling the knob 1336 and sheath 1340 while the pusher 1340 is held stationary to abut the proximal end of the stent 1300 to disengage the stent 1300 from the sheath 1340. As the retention members 1301, 1302 form, the restoring force of the deployment of the retention members 1301, 1302 may adjust the length of the stent 1300 to substantially conform to the length of the ureter as the retention members 1301, 1302 retain the stent 1300 in the kidney and the bladder. An embodiment may include one or more sutures for positioning and stent 1300 retrieval.

In various embodiments, a suture may be removed from a stent (e.g., after deployment) by decoupling ends of the suture, e.g., by cutting, breaking, untying or the like, and proximally pulling on a first end of the suture such that a length of the suture extends through one or more apertures of the stent until a second end of the suture is removed from the stent. One or more sutures may be left coupled to the stent within the patient after deployment. A portion of the suture may extend outside of the patient (e.g., outside the urethra) and may be temporarily adhered to the patient during use to be later manipulated for removal and/or repositioning of the stent (e.g., by pulling on the suture proximally to translate the stent).

In various embodiments, a stent may be delivered antegrade into a patient with a guidewire placed, via a needle, into the kidney and possibly through the ureter into the bladder. The needle may be dilated to accommodate the stent and/or a sheath can be used about the needle and/or stent. The stent can be delivered as similarly described herein with a distal retention member in the bladder and the proximal retention member in the kidney. One or more sutures may extend out of the urethra and/or out of the entry point in the flank through which the stent is delivered.

Various embodiments of the present disclosure include controlled extension stents, particularly ureteral stents. Such stents may have a body made up of a single filament coiled about an axis along the length of the stent or multiple filaments wound in adjacent groups of coils that define a lumen about a longitudinal axis of the stent. Adjacent coils of a single filament or adjacent groups of coils with multiple filaments may be in substantial contact with other adjacent coils or with neighboring adjacent groups in a non-extended state and may be separated in an extended state. In one or more embodiments, a controlled extension stent may have groups of wound coils or coils of a single filament tacked together on a contact line created by the coils as they wind along the length of the stent. The winding may be in a helical manner. Tacking may be achieved through heat setting above the softening point of filament materials while the coils are in contact with each other or by a permanent or dissolvable adhesive applied along the contact line or lines. Temperature ranges to achieve tacking are dependent on the materials used. The strength of the tack varies with heating temperature and time. This may be accomplished, for example, in a dry oven, a water bath, or by using an RF generator at low voltage. For example, with ethylene-vinyl acetate (EVA), parameters for heat setting may include a heat temperature of 70-80° C. with a set time of 30 minutes to 4 hours. Adhesive tacking may be accomplished using a coating composition such as polyvinylpyrrolidone (PVP). Dissolution time may vary based on adhesion to the substrate, composition, and curing (crosslinking). Adhesive tacking may also be accomplished via a hard candy shell coating made out of sugar. Tacking may be formed on a contact line along the entire length of a stent or just at certain portions, depending on the desired stent architecture. A stent may include along the length some groups of coils where the filaments are tacked together while other groups of coils are not tacked together. A body may have groups of coils that separate from neighboring adjacent groups in an extended state. In addition to this group separation, the coiled filaments within the groups may separate from each other in an extended state of the stent. Whether the coiled filaments separate from each other within their group or among groups may depend on whether the filaments or groups are tacked together, and if so, how strong the tacking bond is between the filaments. A stronger tacking bond between the filaments may result in a stent with a higher resistance to tensile stress or bending, while a weaker or non-existing tacking bond may result in a more compliant stent when succumbing to tensile stress or bending.

A manner in which a body extends is controllable by various factors in its design. A material selected for each filament may determine its amount of extension. A stiffer material may require more tensile stress to extend, while a more pliable material may extend more easily. Filament materials, dimensions, and processing are discussed in the present disclosure and play a role in the amount of body extension as well as stent flexibility. For example, extension control may be determined by the thickness of each filament. A thicker filament may be more resistant to tensile stress than a thinner one. Filament thickness may range from, for example, about 0.020 inches (0.508 millimeters) to about 0.037 inches (0.940 millimeters). Further control of body extension may be achieved by setting the pitch of the coils relative to the longitudinal axis of the stent. A more acute pitch relative to a longitudinal axis of the stent may more readily extend compared to a more perpendicular pitch. Various ranges of pitch angles of the present disclosure are discussed below. Extension control may also be determined by the processing and type of materials in order to vary the range of stretching that may result under tensile stresses of the stent. The tension with which the coils are wound may also vary the amount of stretching. Examples of filaments may include a variable cross-section along the length, which may be composed of a coextruded inner and outer core of different materials for additional control over extension. Alternatively, the filament may be solid or hollow, and the radial or hoop strength of the coils may be adjusted to control extension. Further control of body extension may be achieved by the number of filaments grouped together along the stent. A greater number of filaments grouped together may provide more resistance to tensile stresses and thus less extension. Additionally, a body designed with more surface contact among the coiled filaments may provide more friction in resistance to tensile stresses which may result in less body extension.

Devices, particularly in the context of a ureteral stent, may have an outer diameter of about 3 French, about 4.8 French, about 5 French, about 6 French, about 7 French, about 9 French, including any half or whole size within that range, and may have an inner lumen diameter of about 0.038 inches (0.0965 cm) to accommodate the profile of standard medical guidewires within the lumen of the stent. Embodiments of the present disclosure for use as ureteral stents may have a non-extended length of about 20 cm to about 35 cm or about 10 cm to about 30 cm, or the like as measured between the retention members or between proximal and distal tubes. Additional extendable length varies based on all of the parameters previously discussed. Patient respiration may extend a ureter about 3 cm to about 5 cm. A maximum extension may be about 10 cm. Excessive extension may be undesirable during removal of the stent from the patient. A patient may experience additional discomfort during stent removal if the stent extends so much as to resemble the removal of a string rather than a controlled length of a body. An extended length of a body and/or a stent may be maintained within a patient by one or more formed retention members, e.g., a distal retention member formed in a kidney and a proximal retention member formed in a bladder may provide resistive forces such that an extended length of a body is maintained in a ureter and/or between the kidney and the bladder. A body of a stent may be non-uniformly extended. For example, a proximal suture may be proximally translated such that coils of a proximal portion of the body are extended while the remainder of the body is not extended or is extended less than the coils of the proximal portion of the body.

A body may be created by winding one or more filaments about a mandrel to form coils defining a lumen for a guidewire, bodily fluid passage, and/or a tubular structure to support ureter function. These coils may provide column strength to prevent buckling and overriding within the patient. This strength may be further increased by tacking the coils and/or filaments together. However, tacking of the coils may be broken with minimal force to provide controlled extension where needed during ureteral movement. The stent may include coils from end to end or may contain sections of coiled and non-coiled filaments. For example, the ends of the stent may include straight filaments or retention members as discussed in the disclosure below.

During stent delivery, it may be desirable that a stent be substantially straight and relatively rigid until it is in position within a patient. Once in position, it may be desirable that the stent be relatively flexible in order to comfortably function when accommodating ordinary movement of the patient's anatomy. For example, about 3 cm of ureter movement may occur during respiration or body movement. Additionally, ureter length may vary from patient to patient, and so an extension length of up to about 10 cm may be desirable. The addition of a coating to a stent may be desirable to achieve this transition from more rigid to more flexible and is intended to deliver the stent more as a column and dissolve away to leave the more flexible underlying stent.

Devices, systems, and methods of the present disclosure may be used alone or together with other devices, systems, and methods of stent delivery. Exemplary devices, systems, and methods with which embodiments of the present disclosure may be implemented include, but are not limited to, those described in U.S. patent application Ser. No. 15/802, 863 which is herein incorporated by reference in its entirety and for all purposes. Exemplary embodiments, devices, features or otherwise described therein may be incorporated with or into embodiments of the present disclosure.

Materials of a stent may be polymeric in various embodiments of the present disclosure. Polymeric materials suitable for embodiments of the filament may comprise any polymer or polymer blend suitable for use in implantable or insertable medical devices. Polymers may be selected, for example, from suitable members of the following, among others: Percuflex™, C-flex®, polyethene, polyurethane, nylon, polyolefins such as polyethylenes (e.g., metallocene catalyzed polyethylenes), polypropylenes and polybutylenes; polyolefin copolymers, e.g., ethylenic copolymers such as ethylene vinyl acetate (EVA) copolymers, ethylene-methacrylic acid copolymers and ethylene-acrylic acid copolymers, where some of the acid groups can be neutralized with either zinc or sodium ions (commonly known as ionomers); vinyl aromatic polymers such as polystyrene; vinyl aromatic copolymers such as copolymers of olefins and styrene or alpha-methyl styrene, for example, butadiene-styrene copolymers and copolymers of polyisobutylene with polystyrene or polymethylstyrene, for example, polystyrene-polyisobutylene-polystyrene triblock copolymers; polyacetals; chloropolymers such as polyvinyl chloride (PVC); fluoropolymers such as polytetrafluoroethylene (PTFE); polyesters such as polyethyleneterephthalate (PET); polyester-ethers; polyamides such as nylon 6 and nylon 6,6; polyethers; polyamide ethers such as polyether block amides (PEBA) comprising (a) nylon blocks, for example, nylon 6, nylon 4/6, nylon 6/6, nylon 6/10, nylon 6/12, nylon 11 or nylon 12 blocks and (b) polyether blocks, for example, poly(ethylene oxide), poly(trimethylene oxide), poly(propylene oxide) or poly(tetramethylene oxide) blocks, one specific example of which is a poly(tetramethylene oxide)-b-polyamide-12 block copolymer, available from Elf Atochem as PEBAX®; polyoctenamers such as Vestenamer® from Degussa Corp., Parsippany, N.J., which is a mixture of cyclic and linear polyoctenamers; elastomeric and thermoplastic polyurethanes, including polyurethane copolymers (including block and random copolymers that are polyether based, polyester based, polycarbonate based, aliphatic based, aromatic based and mixtures thereof), commercially available examples of which include Carbothane®, Tecoflex®, Tecothane®, Tecophilic®, Tecoplast®, Pellethane®, Chronothane® and Chronoflex®); and vinyl aromatic polymers and copolymers; silicones; polycarbonates; as well as mixtures of any of the foregoing, among others. The filaments may be made up of multiple layers of material for their properties (such as anti-encrustation, radiopacity, etc.). The filaments may be made up of differing materials from each other, may include coextensions of different materials, or may include an inner core and one or more outer layers of different materials. Selecting materials for a stent with increased rigidity will increase a spring coefficient of coils of a body, increasing the body's resistance to extensional forces.

EVA copolymers are one preferred group of polymers for use in ureteral stents. Examples include EVA copolymers having a vinyl acetate content of from about 5% to about 40% (including 5% to 10% to 15% to 20% to 25% to 30% to 35% to 40%, with 10-30% being typical). Increasing the vinyl acetate content typically results in a softer material, while decreasing the vinyl acetate content typically produces a harder material.

The stent of various embodiments of the present disclosure may also contain one or more optional additives, for example, selected from therapeutic agents, radiopaque agents, colorants, other optional additives such as plasticizers and extrusion lubricants, and combinations of the above, among others, in amounts effective to serve their intended purposes. Where used in the devices of the present disclosure, such optional additives may be present, for example, in the polymeric materials such as those discussed above, among others, or in coatings applied to the polymeric materials, or both.

Radiopaque agents facilitate viewing of the stent during insertion and at any point while the stent is implanted. Radiopaque agents useful in the stents of the present disclosure include bismuth salts such as bismuth subcarbonate, bismuth oxychloride, bismuth trioxide, barium sulfate, tungsten, and mixtures thereof. More specific examples of such radio-opaque agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodamide sodium, and meglumine, among others. Where present, the radiopaque agent is typically present in an amount of from about 10% to about 40% (including 10% to 15% to 20% to 25% to 30% to 35% to 40%, with 15-30% being more typical). Additionally, or alternatively, the polymeric material or additive material choice, as well as extrusion technique, may be optimized to enhance device contrast using ultrasound imaging. The incorporation of sonographic agents, in addition to or as an alternative to radiopaque agents, such as contrast beads or foams, among other examples, facilitate viewing of the stent under ultrasonic imaging during insertion of the device and at any point while the device is implanted. One skilled in the art can readily determine an appropriate radiopaque and sonographic agent content to achieve the desired visibility. The polymer materials described may be mixed with the radiopaque and/or the sonographic agents above, or a colorant. A colorant may be used as a visual cue to a medical professional about the location of the stent in the patient.

Drainage elements may be arranged along an exterior of the stent and in fluid communication with the lumen created by the coils of the stent to facilitate drainage of fluid along the interior and exterior of the device. If the filaments are hollow, then the elements may be holes or other shapes. Also, the spacing between coils of the stent may provide for drainage. Additionally or alternatively to the drainage elements, channels may be included on the exterior to increase the drainage capabilities of the device. Channels may assume various shapes and configurations, such as semicircular, triangular, rectangular and trapezoidal cross-sections, respectively, among many other shapes. The above embodiments may also include segmented sections of coiled filaments alternating with sections of straightened filament. Additionally, or in the alternative, the filaments may be formed with a braided pattern with enough structure to form a stent but also loose enough to allow for some degree of controlled extension. Even a relatively tight braided pattern may allow for some extension from the elastic and/or plastic deformation of the filament material.

Various retention members of stents according to one or more embodiments of the present disclosure may be formed by winding the one or more filaments of the elongate tubular body on a mandrel, shaping, and heat setting end portions of the body in a particular form to give the end portions memory when unconstrained in the patient to assume the form of the retention member. A retention member (such as a renal retention member) may comprise a single pigtail wound in a plane that is offset from the plane that is parallel to the longitudinal axis of an intermediate portion of the stent. A polymer of a retention member may be heat set, e.g., with heated water to transition the polymer to a curved pigtail configuration, to have a shape-memory such that the retention member may return to the curved configuration when not extended, e.g., by a guide wire. Other examples of retention members for use with this or other embodiments of the present disclosure include, for example, annular tails, spirals, helixes, coils, corkscrews, malecots, barbs, mushrooms and hook ends, conical shapes, curves, J-shaped curves, among others. The retention member may be a funnel or cone-like shape at the distal end of the stent where the stent diameter gradually enlarges from the proximal end of the stent towards the distal end of the stent. The end portions forming the retention members may be filaments as they occur along the body of the stent or the filaments may be fused together and then given the form of the retention member. A filament or filaments may be formed into a desired shape by heating while on the mandrel. Alternatively, the filament or a grouping of filaments may be laid into a plate having a groove cut into it in the shape of the desired retention member. The plate may be heated from below (for example, with a heat lamp) to form the filament or stent body into a retention member shape according to the configuration of the groove. Both retention members may be formed at the same time using two adjacent plates, each with a groove for the retention member at either end of the stent. The plates may be heated at different temperatures, to the extent necessary, for example, if the two ends of the device are made from different material(s) and may be heated for the same or different lengths of time.

A radiopaque or sonographic band, filler or other marker as part of a stent and/or a delivery device allows a medical professional to view the stent and/or delivery device on a fluoroscope or using ultrasound. Additionally, if the stent is radiopaque or sonovisible, placement of the stent in the patient may be confirmed by viewing the stent on a fluoroscope or using ultrasound.

In various embodiments, parts of a delivery device may include a cannula, a pusher, a catheter, a sheath, and/or a Tuohy-borst or other adapter. These parts may be reversibly coupled to each other, e.g., a locking knob, a wing nut, a detent, a hook, a latch, a cam, a screw, a handle, or the like. These parts may have lengths or distances between ends of the parts that substantially match a length of a stent, a length of a portion of a part engaging a stent (e.g., about 5 mm, about 10 mm, or the like), or a length of an anatomy of a patient. For example, a pusher may be about 40 cm long. Parts may be made up of various materials such as a polymer, nylon, polyethene, polyurethane, Ultem®, polyetherimide, polyether ether ketone, polyethylene terephthalate, polypropylene, polycarbonate, a stainless-steel, an alloy, or the like. Distal portions of parts may be angularly cut (e.g., such that a distal end of one part may be guided within a lumen of another part or guided within a stent) or may be square cut (e.g., such that square cuts of two parts or a part and a stent may abut each other for pushably translating with each other).

Methods of treating a patient with embodiments of the present disclosure may be performed by introducing a stent in accordance with the above, additional, or alternative embodiments into a patient. A physician may use a cystoscope to locate the ureteral orifice where urine drains into the bladder. This may or may not be performed over an already introduced flexible guidewire, of which the stent may slide over via the lumen of the stent created by the coils of one or more filaments along the length of the stent. X-ray or fluoroscopy imaging may be used to monitor the guidewire and/or stent into the ureteral orifice and up the ureter. Contrast fluid may be injected to improve guidance. If a guidewire is used, the stent may be pushed over and along the guidewire and up into the kidney. Advancing the stent may be performed by using a delivery device. If a guidewire is used, it may be removed before or after the stent is in position. A retention member of a stent, if present at one or both ends of the stent, may be formed in the kidney and/or bladder. The stent may be positioned within a patient such that the stent cooperatively extends according to the length of the ureter and/or extends and contracts along with the bodily movement of the patient without migrating out of position.

A method for positioning a stent may include inserting a guidewire to a target position within a patient, e.g., a kidney. A stent comprising a body comprising coils may be inserted over the guidewire and/or a cannula. The stent may be distally translated within the patient over the guidewire via a pusher. The stent may be proximally translated within the patient over the guidewire via a first suture associated with a distal portion of the stent. The stent may be positioned within the body by translating a pusher, a cannula, a sheath, and/or a guidewire. Portions of a stent delivery system may be manipulated by one or more handles or knobs that may be reversibly locked to each other. The stent may be removed from the patient via translation of a second suture disposed through a proximal portion of the stent. The stent may be distally translated by pushing the stent with the pusher. The stent may be proximally translated by applying tension to the first suture. The stent may be translated by compressing a gap between adjacent coils of the sent such that a diameter of a lumen of the adjacent coils about the guidewire increases. A length of the stent within the patent may be adjusted by adjusting a gap between select body wound coils of the stent. A length of the stent may be adjusted in response to observation of a position of the stent within the patient by adjusting a tension of a plurality of coils of the stent. For example, the second suture may be proximally pulled to extend a body of the stent. The first suture may be cut and may be withdrawn from the patient.

Variations, modifications, and other implementations of the present disclosure in addition to the various embodiments described herein will occur to those of ordinary skill in the art. Accordingly, the present disclosure is to be defined not by the preceding illustrative description but instead by the following claims:

What is claimed is:

1. A stent, comprising:
    a body comprising coils about a longitudinal axis of the stent and along the length of the stent between a proximal end and a distal end in a substantially helical pattern, the coils defining a lumen along the longitudinal axis through the center of the body;
    a distal tube having a wall extending distally from the distal end of the body, wherein the lumen extends through the distal tube;
    a first aperture extending through the wall of the distal tube into the lumen;
    a proximal tube having a wall extending proximally from the proximal end of the body, wherein the lumen extends through the proximal tube;
    a distal retention member extending distally from the distal tube, wherein the lumen extends through the distal retention member;
    a proximal retention member having a wall extending proximally from the proximal tube to a proximal end of the proximal retention member, wherein the lumen extends through the proximal retention member to the proximal end of the proximal retention member; and
    a distal suture having a first end, a second end, and a mid-portion, wherein the mid-portion extends through the first aperture, and the suture extends proximally along the body from the mid-portion to the first end and the second end proximal to the proximal tube.

2. The stent of claim 1, further comprising a second aperture extending through the wall of the distal tube into the lumen such that the first aperture and the second aperture are aligned forming a suture axis that is offset from the longitudinal axis, and wherein the mid-portion of the distal suture extends through the second aperture.

3. The stent of claim 1, further comprising:
    an aperture extending through the wall of the proximal retention member into the lumen; and
    a proximal suture having a first end, a second end, and a mid-portion, wherein the mid-portion extends through the aperture extending through the wall of the proximal retention member and through the proximal end of the proximal retention member.

4. The stent of claim 1, wherein a portion of the distal suture is adhered to the proximal tube.

5. The stent of claim 1, further comprising a pre-set gap between select adjacent coils of the body, wherein the gap is configured such that a diameter of the lumen increases as the select adjacent coils are compressed together along the longitudinal axis.

6. The stent of claim 1, wherein axial compression of the body is controllable by applying proximal tension to the distal suture.

7. The stent of claim 1, wherein the proximal and distal retention members are in the shape of a pigtail, a J-shaped curve, a cope loop, a spiral shape, a helical shape, or a cork screw, or a combination thereof.

8. The stent of claim 1, wherein the distal retention member has a tapered distal tip, tapering distally.

9. A stent, comprising:
    a body comprising coils about a longitudinal axis of the stent and along the length of the stent between a proximal end and a distal end in a substantially helical pattern, the coils defining a lumen along the longitudinal axis through the center of the body;
    a distal tube having a wall extending distally from the distal end of the body, wherein the lumen extends through the distal tube;
    a first aperture extending through the wall of the distal tube into the lumen;
    a proximal tube having a wall extending proximally from the proximal end of the body, wherein the lumen extends through the proximal tube;
    a distal retention member extending distally from the distal tube, wherein the lumen extends through the distal retention member;
    a proximal retention member having a wall extending proximally from the proximal tube to a proximal end of the proximal retention member, wherein the lumen extends through the proximal retention member to the proximal end of the proximal retention member; and
    a distal suture having a first end, a second end, and a mid-portion, wherein the mid-portion extends through the first aperture;
    wherein axial compression of the body is controllable by applying proximal tension to the distal suture.

10. The stent of claim 9, further comprising a pre-set gap between select adjacent coils of the body, wherein the gap is configured such that a diameter of the lumen increases as the select adjacent coils are compressed together along the longitudinal axis.

11. The stent of claim 9, further comprising a second aperture extending through the wall of the distal tube into the lumen such that the first aperture and the second aperture are aligned forming a suture axis that is offset from the longitudinal axis, and wherein the mid-portion of the distal suture extends through the second aperture and the first end and the second end of the suture are positioned proximal to the proximal tube.

12. The stent of claim 9, wherein the suture extends from a distal end of the body to the proximal end of the body.

13. The stent of claim 9, wherein the suture extends from the distal end of the body proximally along a suture axis that is offset from the longitudinal axis of the stent.

* * * * *